(12) United States Patent
Zhou et al.

(10) Patent No.: US 12,082,910 B2
(45) Date of Patent: Sep. 10, 2024

(54) MINIATURIZED NONINVASIVE GLUCOSE SENSOR AND CONTINUOUS GLUCOSE MONITORING SYSTEM

(71) Applicant: MEDTRONIC MINIMED, INC., Northridge, CA (US)

(72) Inventors: Li Zhou, Pasadena, CA (US); Raymond M. Russell, Arcadia, CA (US); Peter Schultz, Chatsworth, CA (US); Anuj M. Patel, Porter Ranch, CA (US); Carol Chen, La Puente, CA (US); Roshanne Malekmadani, Los Angeles, CA (US); Lynette To, Sherman Oaks, CA (US); Hsiao-Yu S. Kow, Ladera Ranch, CA (US); Raghavendhar Gautham, Northridge, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 936 days.

(21) Appl. No.: 16/942,721

(22) Filed: Jul. 29, 2020

(65) Prior Publication Data
US 2020/0352450 A1   Nov. 12, 2020

Related U.S. Application Data

(63) Continuation-in-part of application No. 16/274,082, filed on Feb. 12, 2019, now abandoned.

(51) Int. Cl.
*A61B 5/00* (2006.01)
*A61B 5/145* (2006.01)

(52) U.S. Cl.
CPC ........ *A61B 5/0095* (2013.01); *A61B 5/14532* (2013.01); *A61B 5/7267* (2013.01)

(58) Field of Classification Search
CPC .. A61B 5/0095; A61B 5/14532; A61B 5/7267
See application file for complete search history.

(56) References Cited

U.S. PATENT DOCUMENTS

| 4,691,714 A | 9/1987 | Wong et al. |
| 4,755,173 A | 7/1988 | Konopka et al. |

(Continued)

FOREIGN PATENT DOCUMENTS

| CN | 105559794 A | 11/2016 |
| WO | 2022026062 A1 | 2/2022 |

OTHER PUBLICATIONS

Geng Zhanxiao, et al., Noninvasive Continuous Glucose Monitoring Using a Multisensor-Based Glucometer and Time Series Analysis, Scientific Reports, vol. 7, No. 1, Dec. 1, 2017, XP055837335, DOI: 10.1038/s41598-017-13018-7, Retrieved from the Internet: https://www.nature.com/articles/s41598-017-13018-7.pdf.

(Continued)

*Primary Examiner* — Alex M Valvis
*Assistant Examiner* — Justin Xu
(74) *Attorney, Agent, or Firm* — Weaver Austin Villeneuve & Sampson LLP

(57) ABSTRACT

Systems and methods are described herein for utilizing a photoacoustic sensor for estimating analyte concentration levels. Also described here are training methods for training an analyte sensor to more accurately estimate an analyte concentration level on the basis of a received acoustic signal.

20 Claims, 25 Drawing Sheets

(56) References Cited

U.S. PATENT DOCUMENTS

| | | |
|---|---|---|
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 11,116,448 B1 | 9/2021 | Trapero Martin et al. |
| 2003/0135100 A1* | 7/2003 | Kim ............ A61B 5/1486 600/365 |
| 2004/0039271 A1 | 2/2004 | Blank et al. |
| 2007/0123819 A1 | 5/2007 | Mernoe et al. |
| 2007/0197886 A1 | 8/2007 | Naganuma et al. |
| 2007/0206193 A1 | 9/2007 | Pesach |
| 2008/0275319 A1 | 6/2008 | Van Gogh et al. |
| 2009/0079977 A1 | 3/2009 | Lipson et al. |
| 2010/0160861 A1 | 6/2010 | Causey, III et al. |
| 2012/0271188 A1 | 10/2012 | Van Kesteren |
| 2013/0211204 A1 | 8/2013 | Caduff et al. |
| 2013/0237802 A1 | 9/2013 | Irisawa |
| 2014/0026639 A1 | 1/2014 | Wang et al. |
| 2014/0266399 A1 | 9/2014 | Corman et al. |
| 2015/0119667 A1 | 4/2015 | Reihman et al. |
| 2015/0208924 A1 | 7/2015 | Li et al. |
| 2016/0081597 A1 | 3/2016 | Bhavaraju et al. |
| 2017/0119255 A1 | 5/2017 | Mahajan et al. |
| 2017/0128722 A1* | 5/2017 | Perez ............ A61B 5/021 |
| 2017/0332914 A1 | 11/2017 | Chapman et al. |
| 2018/0238794 A1 | 8/2018 | Kangas et al. |
| 2019/0159705 A1 | 5/2019 | Sim et al. |
| 2019/0261900 A1* | 8/2019 | Tang ............ G01N 27/026 |
| 2020/0029870 A1* | 1/2020 | Jung ............ A61B 5/14535 |
| 2020/0253513 A1 | 8/2020 | Zhou et al. |
| 2020/0352482 A1 | 11/2020 | Gal et al. |
| 2020/0352484 A1 | 11/2020 | Zhou et al. |
| 2021/0052164 A1 | 2/2021 | Shnaiderman et al. |
| 2022/0257154 A1 | 8/2022 | Zhou et al. |

OTHER PUBLICATIONS

Jernelv Ine L., et al., A Review of Optical Methods for Continuous Glucose Monitoring, Applied Spectroscopy Reviews, vol. 54, No. 7, Aug. 9, 2019, pp. 543-572, XP055837301, US ISSN: 0570-4928, DOI: 10.1080/05704928.2018.1486324, Retrieved from Internet: https://www.tandfonline.com/doi/pdf/10.1080/05704928.2018.1486324?needAccess=true.

International Search Report and Written Opinion dated Sep. 13, 2021, in Application No. PCT/US2021/036906 [MEDTP035X1WO].

U.S. Final office Action dated Feb. 1, 2022, in U.S. Appl. No. 16/274,082.

U.S. Non-Final office Action dated Jun. 28, 2021, in U.S. Appl. No. 16/274,082.

U.S. Non-Final Office Action dated Oct. 20, 2023, in U.S. Appl. No. 17/734,245 [MEDTP035C1US].

U.S. Final Office Action dated Apr. 2, 2024, in U.S. Appl. No. 17/734,245 [MEDTP035C1US].

U.S. Non-Final Office Action dated Dec. 8, 2023 in U.S. Appl. No. 16/942,719.

* cited by examiner

MINIATURIZED NONINVASIVE GLUCOSE SENSOR AND CONTINUOUS GLUCOSE MONITORING SYSTEM

CROSS-REFERENCE TO RELATED APPLICATION

This application is a continuation-in-part application of U.S. application Ser. No. 16/274,082, filed on Mar. 7, 2019.

TECHNICAL FIELD

Embodiments of the subject matter described herein relate generally to photoacoustic techniques for monitoring analyte concentration levels. More particularly, embodiments of the subject matter described herein relate to photoacoustic techniques for monitoring blood glucose concentration levels of a user.

BACKGROUND

There are approximately 450 million people suffering from diabetes worldwide. As is known, diabetes is a result of the body's inefficient production or use of insulin, which leads to medical complications of hyper- or hypo-glycemia in the short term, and micro- or macro-vascular problems in the long term if left untreated. The control of blood glucose concentration levels to within a desired range, for example through the administration of insulin, is therefore necessary to prevent the development of such complications.

In order to determine when blood glucose concentration levels need to be controlled, it is necessary to measure the blood-glucose concentration levels of a diabetic person.

Photoacoustic techniques for monitoring glucose concentration levels are desirable for several reasons. In particular, photoacoustic techniques do not require an invasive component, such as a transdermal sensor probe or a "finger prick" puncture, in order to monitor the glucose concentration levels of a user. Due to the non-invasive nature of photoacoustic techniques, it is possible to increase user comfort whilst wearing the device and also to improve the ease and comfort of installation of the device. Furthermore, it is possible to continuously measure the blood glucose concentration level with photoacoustic methods, in contrast to the less-useful intermittent monitoring realized by "finger-prick" monitoring techniques.

Photoacoustic techniques rely upon the irradiation of a target with light, such as light provided by a laser beam. The light produces thermal effects, such as a volumetric expansion, in the target and the thin layer of air contacting the target due to thermal diffusion, which causes a pressure oscillation that generates an acoustic wave. The characteristics of this acoustic wave depend upon several factors, such as the target's absorption co-efficient to the wavelength of light used, the density of the medium through which the acoustic wave propagates, the thermal expansion co-efficient of the target, the velocity of the acoustic wave, and so on.

If skin is used as a target, the light may penetrate a distance into the skin and excite molecules, such as glucose molecules, beneath the skin. The acoustic wave generated by the thermal excitation (and subsequent volumetric expansion) of these glucose molecules can be used to estimate the concentration of the glucose molecules.

However, there are disadvantages associated with the use of photoacoustic techniques for monitoring blood glucose concentration levels. In particular, the acoustic wave generated through the excitation of glucose molecules may not be of sufficient magnitude to obtain a strong enough signal for the accurate measurement of the blood glucose concentration. Furthermore, the characteristics of the acoustic wave may vary from person to person, dependent upon (for example) the user's skin light transmittivity characteristics, skin sweat gland activity, skin composition and structure, and so on.

Accordingly, it is desirable to overcome the disadvantages associated with photoacoustic techniques for measuring analyte concentrations, such as blood glucose concentration levels. Furthermore, other desirable features and characteristics will become apparent from the subsequent detailed description and the appended claims, taken in conjunction with the accompanying drawings and the foregoing technical field and background.

BRIEF SUMMARY

According to a first aspect, there is provided an analyte monitor. The analyte monitor includes a light emitter configured to emit light at a target. The analyte monitor includes a sensor configured to sense acoustic waves generated by analyte molecules in the target in response to the emitted light. The analyte monitor also includes a resonance chamber sized to form a standing wave with the generated acoustic waves. The analyte monitor includes a signal processor configured to estimate an analyte concentration level on the basis of the sensed acoustic waves.

In an embodiment, the light emitter is configured to emit light having a wavelength in the mid-infrared region.

In an embodiment, the sensor is positioned proximate to an anti-node of the standing wave to be formed in the resonance chamber.

In an embodiment, the signal processor is configured to determine whether the estimated analyte concentration level falls within one of two or more pre-determined ranges. Preferably, the analyte monitor further comprises a transmitter configured to transmit a signal when the estimated analyte concentration level falls within one of the two or more pre-determined ranges.

In an embodiment, the sensor comprises a microphone. In an alternative embodiment, the sensor comprises a transducer.

In an embodiment, the resonance chamber comprises a resonance branch for formation of the standing wave and a measurement branch connecting the resonance branch to the sensor, the measurement branch being positioned proximate to an anti-node of the standing wave to be formed in the resonance branch.

According to a second aspect, there is provided a method for training an algorithm for estimating analyte concentration levels of a specific target from acoustic signals generated via thermal vibration of analyte molecules in the target in response to irradiation of the target with light. The method includes the step of obtaining acoustic signals with a sensor of a first analyte monitor and simultaneously obtaining analyte concentration levels using a reference analyte monitor to form a training set, the reference analyte monitor and the first analyte monitor being different. The method includes the step of training an algorithm of a signal processor of the first analyte monitor using features of the obtained acoustic signals and the obtained analyte concentration levels of the training set. The method also includes the step of, after training of the algorithm, using the first analyte monitor to estimate analyte concentration levels from obtained acoustic signals.

In an embodiment, the reference analyte monitor is a continuous glucose monitor having an invasive component and the first analyte monitor is non-invasive.

In an embodiment, the features of the obtained acoustic signals are selected from the group comprising: a timestamp of the recording acoustic signal; an amplitude of the acoustic signals, an in-phase component of the acoustic signals; and out-of-phase component of the acoustic signals; and a frequency of the acoustic signals.

In an embodiment, the step of using the first analyte monitor to estimate analyte concentration levels from obtained acoustic signals comprises determining whether an estimated value of the analyte concentration level falls within two or more pre-determined ranges.

In an embodiment, the method further includes a step of determining a confidence level that the analyte concentration level falls within one of the two or more pre-determined ranges.

In an embodiment, the method further includes transmitting, using a transmitter, a signal in response to a determination that the estimated value of the analyte concentration level falls within one or more of the two or more pre-determined ranges. Preferably, the signal is a blood glucose concentration pre-determined range value or an alert signal.

In an embodiment, the analyte molecules are glucose molecules.

In an embodiment, the step of using the first analyte monitor to estimate concentration levels from obtained acoustic signals comprises amplifying and filtering of the obtained acoustic signal. Preferably, at least part of the amplifying and filtering of the obtained acoustic signal is performed using a resonance chamber.

In an embodiment, the method additionally includes the steps of converting the obtained acoustic signals into an analog electrical signal using a sensor; and converting the analog electrical signal into a digital electrical signal using an analog-to-digital converter.

According to a third aspect, there is provided a computer-readable medium containing instructions which, when executed by a processor, performs a method for training an algorithm for estimating analyte concentration levels of a specific target from acoustic signals generated via thermal vibration of analyte molecules in the target in response to irradiation of the target with light. The method includes the step of obtaining acoustic signals with a sensor of a first analyte monitor and simultaneously obtaining analyte concentration levels using a reference analyte monitor to form a training set, the reference analyte monitor and the first analyte monitor being different. The method includes the step of training an algorithm of a signal processor of the first analyte monitor using features of the obtained acoustic signals and the obtained analyte concentration levels of the training set; and after training of the algorithm, using the first analyte monitor to estimate analyte concentration levels from obtained acoustic signals.

According to a fourth aspect, there is provided a photoacoustic method for estimating analyte concentration levels in a target. The method includes the step of measuring an impedance of the target via electrical impedance spectroscopy. The method also includes the steps of irradiating, with a light emitter, the target with light and obtaining, with a sensor, a primary acoustic signal generated by the target in response to the irradiation of the target with light of the first wavelength. The method then includes the step of estimating an analyte concentration level in the target based on both of the obtained primary acoustic signal and the measured impedance of the target.

According to a fifth aspect, there is provided a photoacoustic method for estimating analyte concentration levels in a target. The method includes the step of applying, using a heating element, heat to the target. The method then includes the step of measuring, with a thermal sensor, a thermal response of the target to the applied heat. The method then includes the steps of irradiating, with a light emitter, the target with light of a first wavelength and obtaining, with a sensor, a primary acoustic signal generated by the target in response to the irradiation of the target with light of the first wavelength. The method then includes the step of estimating an analyte concentration level in the target based on both of the obtained primary acoustic signal and the measured thermal response.

According to a sixth aspect, there is provided a photoacoustic method for estimating analyte concentration levels in a target. The method includes the steps of irradiating the target with light of a first wavelength and obtaining, with a sensor, a primary acoustic signal generated by the target in response to the irradiation of the target with light of the first wavelength. The method also includes the steps of irradiating the target with light of a second wavelength and obtaining, with a sensor, a secondary acoustic signal generated by the target in response to the irradiation of the target with light of the second wavelength. The method also includes the step of estimating, on the basis of the obtained secondary acoustic signal, a background absorption level of light. The method also includes the step of estimating an analyte concentration level in the target based on both of the obtained primary acoustic signal and the estimated background absorption level of light.

According to a seventh aspect, there is provided an analyte monitor. The analyte monitor comprises a light emitter configured to emit light of a first wavelength toward a target and a sensor configured to sense acoustic waves generated by analyte molecules in the target in response to the light having the first wavelength emitted by the light emitter. A primary acoustic signal is generated by the sensor on the basis of the sensed acoustic waves. The analyte monitor additionally includes a voltage controller and first and second electrodes arranged to be placed into contact with the target to apply a voltage to the target. The analyte monitor additionally includes an impedance sensor module to determine an impedance of the target on the basis of the applied voltage. The analyte monitor additionally includes a signal processor configured to estimate an analyte concentration level on the basis of both the primary acoustic signal sensed by the sensor and an impedance determined by the impedance sensor module. In an embodiment, the analyte monitor additionally or alternatively includes a heating element configured to apply heat to the target and a thermal sensor to measure a thermal response of the target to applied heat, wherein the signal processor estimates the analyte concentration level additionally on the basis of the measured thermal response. Additionally or alternatively, the light emitter may emit light of a second wavelength toward the target, the first wavelength and the second wavelength being different, and wherein the signal processor estimates a background absorption level of light on the basis of acoustic waves sensed by the sensor in response to the emission of light of the second wavelength, and wherein the signal processor estimates the analyte concentration additionally on the basis of the estimated background absorption level of light.

According to an eighth aspect, there is provided an analyte monitor. The analyte monitor includes a light emitter configured to emit light of a first wavelength toward a target and a sensor configured to sense acoustic waves generated by analyte molecules in the target in response to the light emitted by the light emitter. A primary acoustic signal is generated by the sensor on the basis of the sensed acoustic waves. The analyte monitor also includes a heating element configured to apply heat to the target and a thermal sensor configured to measure a thermal response of the target to applied heat. The analyte monitor also includes a signal processor configured to estimate an analyte concentration level on the basis of the primary acoustic signal and the measured thermal response.

According to a ninth aspect, there is provided an analyte monitor. The analyte monitor includes a light emitter configured to emit light of a first wavelength and light of a second wavelength toward a target, the first wavelength and the second wavelength being different. The analyte monitor includes a signal processor to estimate a background absorption level of light on the basis of acoustic waves sensed by the sensor in response to the emission of light of the second wavelength. The signal processor also estimates an analyte concentration level on the basis of both the primary acoustic signal and the estimated background absorption level of light.

According to a tenth aspect, there is provided an analyte monitor for estimating analyte concentration levels in a target. The analyte monitor comprises a light emitter configured to emit light toward a target and a sensor configured to sense acoustic waves generated by analyte molecules in the target in response to the light emitted by the light emitter. The sensor generates a primary acoustic signal on the basis of the sensed acoustic waves. The analyte monitor further comprises a voltage controller and first and second electrodes configured to be placed into contact with the target. a voltage controller configured to bias the electrodes. The analyte monitor further comprises a signal processor configured to estimate an analyte concentration level on the basis of the primary acoustic signal.

According to an eleventh aspect, there is provided a method for estimating analyte concentration levels in a target. The method comprises the steps of emitting light, using a light emitter, toward a target and applying, using first and second electrodes and a voltage controller, a potential bias to the target. The method also includes the step of sensing, using a sensor, acoustic waves generated by analyte molecules in the target in response to the light emitted by the light emitter and generating a primary acoustic signal on the basis of the sensed acoustic waves. The method also includes the step of estimating, using a signal processor, an analyte concentration level on the basis of acoustic waves sensed by the sensor.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
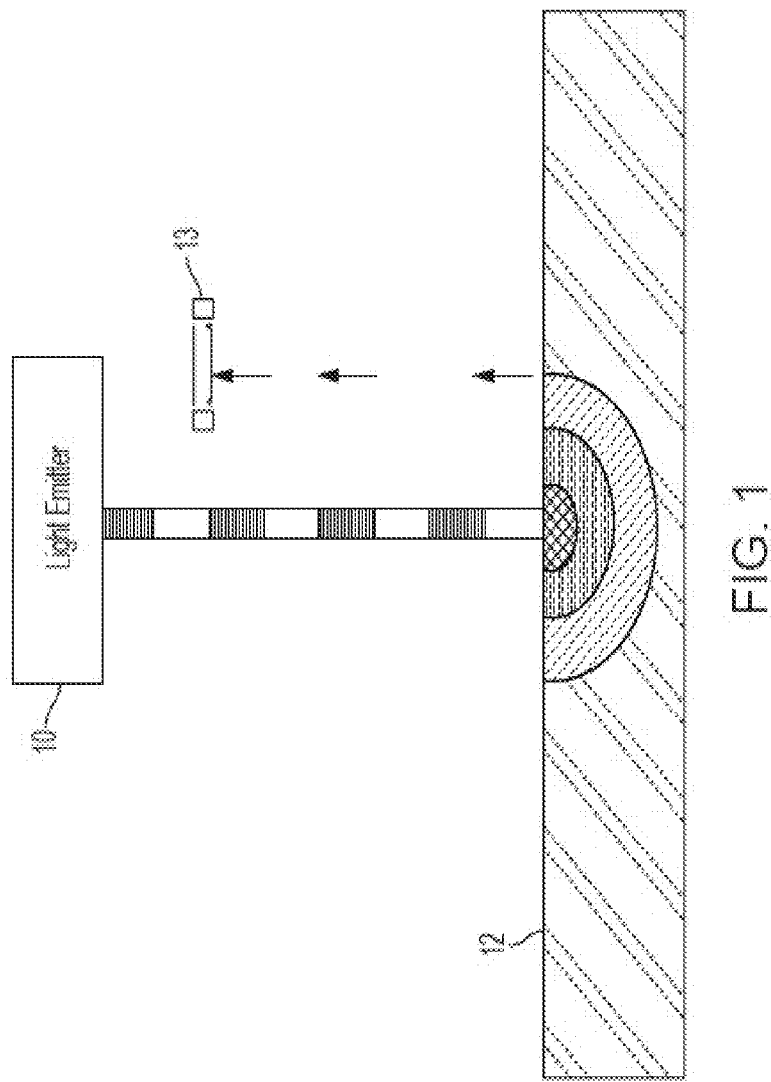
FIG. 1 shows a schematic of a photoacoustic technique for measuring an analyte concentration of a target.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

"Connected/Coupled"—The following description refers to elements or features being "connected" or "coupled" together. As used herein, unless expressly stated otherwise, "coupled" or "connected" means that one element/feature is directly or indirectly joined to (or directly or indirectly communicates with) another element/feature, and not necessarily mechanically.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

For the sake of brevity, conventional techniques related to signal processing, data transmission, signaling, network control, and other functional aspects of the systems (and the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

It should be appreciated that the later-described digital signal processor, and any corresponding logical elements, individually or in combination, are exemplary means for performing a claimed function.

FIG. 1 shows a schematic illustrating how photoacoustic measurement techniques may be used to obtain a sensor signal representative of an analyte concentration, for example a blood glucose concentration level of a user. As can be seen in FIG. 1, a light emitter 10 is configured to emit light towards a target 12, which may be tissue of a user which is covered by skin. The light incident on the target 12 then penetrates a distance into the target 12 and interacts with analyte molecules, for example glucose molecules, present in the target 12. The analyte molecules are thermally excited and vibrate, and the medium surrounding these molecules undergoes a volumetric expansion, thereby generating an acoustic wave. This acoustic wave propagates out of the target 12 and into the medium surrounding the target, for example air. The propagation of the acoustic wave is illustrated in FIG. 1 through the use of bold arrows. The acoustic wave is then detected by a sensor 13 configured to convert the pressure of the acoustic wave into an electrical signal. In an exemplary embodiment, the sensor 13 comprises a microphone. In an alternative exemplary embodiment, the sensor 13 comprises a transducer, for example a piezoelectric transducer.

Figure 2:
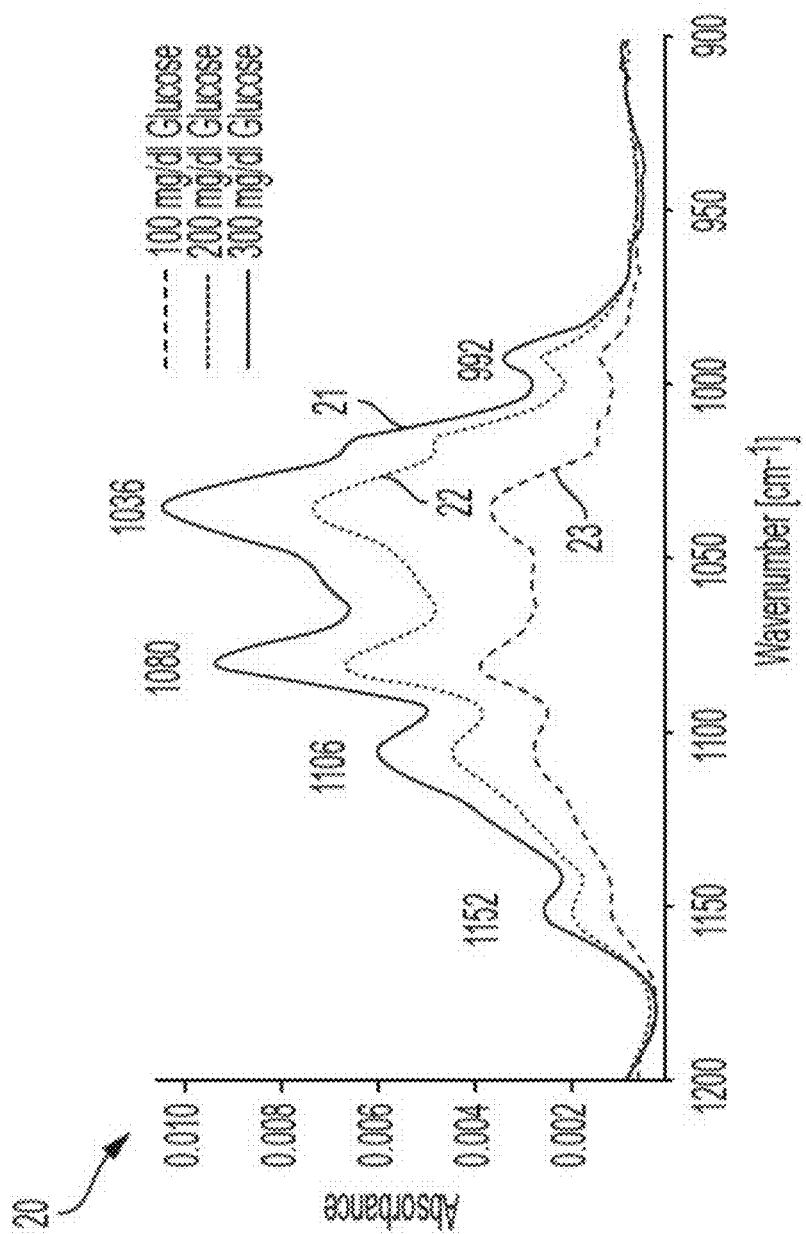
FIG. 2 shows a graph of wavelengths of light that strongly interact with glucose molecules.

In an exemplary embodiment, the wavelength of the light emitted by the light emitter 10 is selected so as to strongly interact with the analyte of interest. As can be seen in the graph 20 shown in FIG. 2, if the analyte of interest is glucose, the wavelength of the light emitted by the light emitter can be selected to correspond to wavelengths which interact strongly with glucose molecules for improved thermal excitation of the glucose molecules. The graph 20 of FIG. 2 shows that wavenumbers (the reciprocal of wavelength) of between about 1000 and 1150 interact strongly with glucose molecules. This range of wavenumbers corresponds to wavelengths of light (8,700 nm to 10,000 nm) in the mid-infrared region.

As can also be seen in FIG. 2, the absorbance of light by glucose molecules in this wavenumber region generally increases as the glucose concentration level increases. The three spectra 21, 22 and 23 shown in the graph 20 relate to the absorbance of light at blood glucose concentration levels of 300 mg/dl, 200 mg/dl and 100 mg/dl, respectively.

In general, the higher the level of absorbance of light by the analyte, the greater the acoustic response signal that will be subsequently generated by the thermal excitation of that analyte. As such, the magnitude of the acoustic response signal after irradiation of the target with light of a particular wavelength can be correlated to the analyte concentration level present in the target.

The present inventors recognized that at certain analyte concentration levels, the magnitude of the acoustic response is not large enough to accurately distinguish between differences in analyte concentrations without the use of highly sensitive, expensive sensors. These types of highly-sensitive sensor may be prohibitively expensive when attempting to commercialize an analyte monitor based on photoacoustic techniques.

In order to circumvent the need for these kinds of expensive sensors to accurately detect the magnitude of the acoustic response from the target, the inventors recognized that the acoustic signal response may be improved through the use of a resonance chamber. A resonance chamber uses the physical principle of resonance to enhance the acoustic response. More specifically, when an acoustic wave enters the resonance chamber, the acoustic wave reflects back and forth within the chamber with minimal energy loss so as to form a standing wave. As additional acoustic waves enter the resonance chamber, the intensity of the standing wave increases.

As such, by pulsing the light emitted from the light emitter 10 and then measuring the intensity of the acoustic standing wave formed in reaction to these light pulses, it is possible to more accurately correlate the acoustic response to an analyte concentration value for a given quality of sensor.

The inventors additionally found that, through the use of a resonance chamber, a certain amount of noise-filtering of the acoustic response was achievable. More specifically, since the resonance chamber is sized so as to form a standing wave with acoustic waves having a specific wavelength of interest, "noise" (acoustic waves of different wavelengths/frequencies) are not amplified by the standing wave in the same manner as the acoustic waves having the wavelength of interest. As such, the resonance chamber not only amplifies the wavelengths of the acoustic waves of interest, but also advantageously acts as a mechanical bandwidth-filter for the acoustic waves of the acoustic response.

Figure 3:
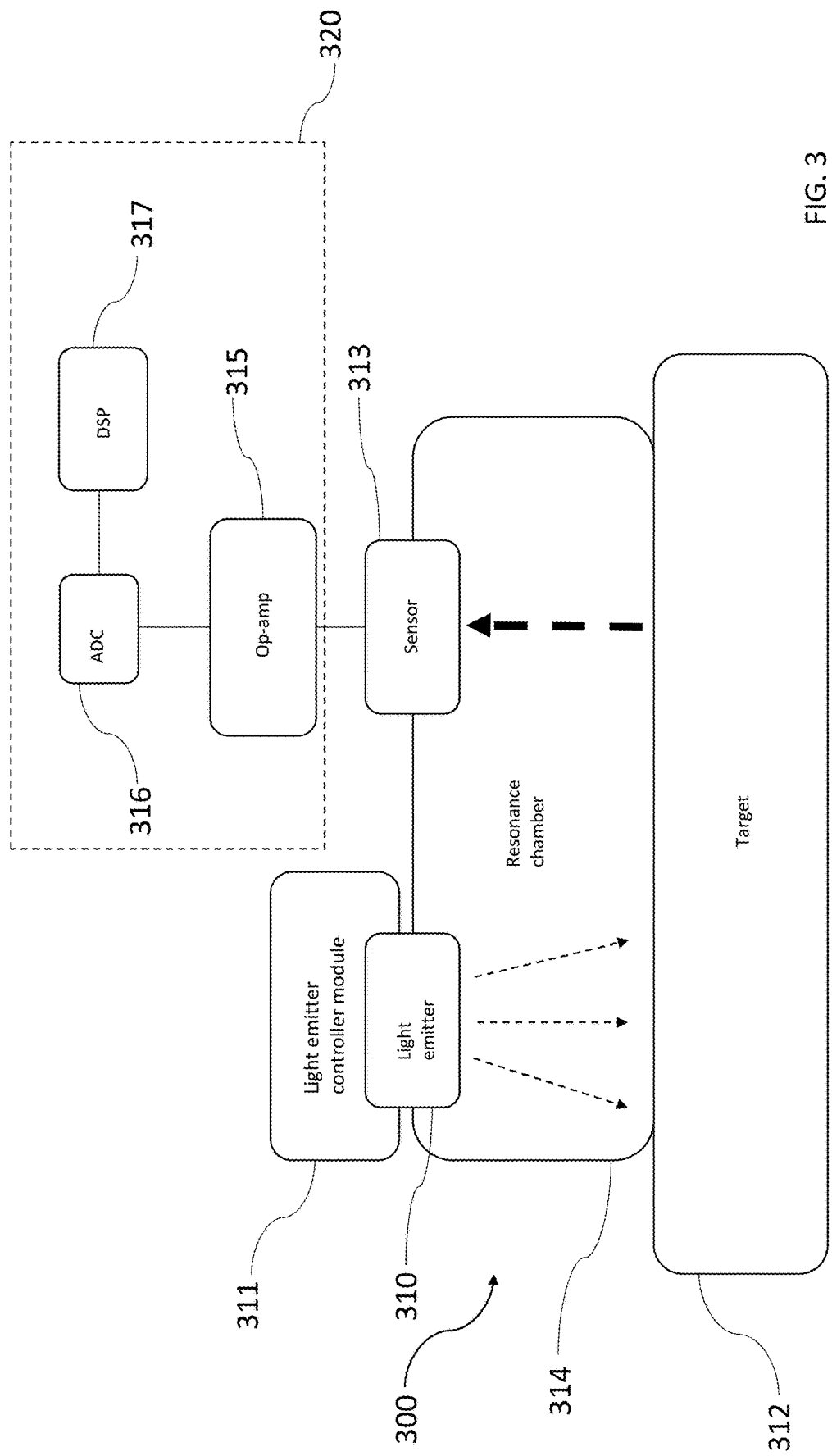
FIG. 3 shows a schematic of an analyte monitor in accordance with exemplary embodiments.

A schematic of an exemplary analyte monitor 300 in accordance with an embodiment is shown in FIG. 3. As can be seen in FIG. 3, the analyte monitor 300 includes a light emitter 310 for emitting light (shown with thin dashed lines) towards a target 312. In an exemplary embodiment, the light emitter 310 comprises a light-emitting diode (LED). In an alternative embodiment, the light emitter 310 comprises a laser chip. A light emitter controller module 311 includes circuitry associated with the light emitter 310. In exemplary embodiments, the light emitter controller module 311 is configured to control the light emitter 10 such that the pulses of light emitted by the light emitter 10 have a pre-determined or a variable pulse repetition frequency (PRF). In other words, the light emitter controller module 311 is suitable for modulating the frequency of the light pulses emitted by the light emitter 310. Preferably, the light emitter controller module 311 is configured to control the light emitter 310 so as to emit light pulses having a duration of about 500 ns per pulse at a frequency of about 50 kHz or more. This pulse duration and frequency has been found to achieve a good acoustic response for certain analytes of interest, such as glucose.

In an embodiment, the light emitter 310 may include a heat conduction element (not shown) configured to conduct heat away from the light emitter 310 so as to reduce the likelihood that the light emitter 310 is heated to an undesirable temperature. In an additional or alternative embodiment, the light emitter 310 may include an anti-reflection surface (not shown) to reduce acoustic signal response noise caused by reflections of the emitted light.

The analyte monitor 300 further includes a sensor 313, for example a microphone or a transducer, such as a piezoelectric transducer. The sensor 313 is configured to detect acoustic waves (shown with a bold dashed line) emitted from the thermal excitation of analyte molecules and volumetric expansion in the target 312 by the light emitted from the light emitter 310 and generate an electrical signal based on these acoustic waves.

The analyte monitor 300 further includes a resonance chamber 314. The resonance chamber 314 is sized and dimensioned so as to form a standing wave for acoustic waves having a wavelength corresponding to the wavelength of acoustic waves generated through the volumetric expansion of the analyte-containing medium of interest after irradiation with light, which is controlled by the pulse repetition frequency (PRF). For example, if the analyte of interest was glucose, and the wavelength of the acoustic wave generated through the irradiation of glucose with light at the pulse repetition frequency around 55 KHz was on the order of about 6 mm, then the resonance chamber would be sized and dimensioned to as to support a standing wave having a length of the order of 6 mm. In an embodiment, the resonance chamber has a length that is a scalar multiple of the length of the acoustic wave generated through the thermal excitation and subsequent volumetric expansion of a glucose molecule, for example 6 mm, 12 mm, 18 mm, and so on. It will be appreciated that if the standing wave were to have a different wavelength, the dimensions of the resonance chamber may be changed accordingly. Although the embodiment in FIG. 3 shows the light emitter being inside the resonance chamber, in various embodiments the light emitter is located outside of the resonance chamber.

The present inventors found that, through the use of such a resonance chamber, acoustic wave amplification of up to about three times can be achieved, in comparison to the base acoustic signal. Furthermore, as explained above, the resonance chamber may perform a noise-filtering function.

In exemplary embodiments, the sensor 313 is operably connected to a signal processor 320. In the embodiment shown in FIG. 3, the signal processor 320 includes an operational amplifier ("op-amp") 315 configured to further amplify the electronic signal derived from the acoustic response of the target 312. In exemplary embodiments, the op-amp 315 is operably connected to an analog-to-digital converter 316 configured to convert the analog electrical signal from the sensor 313 to a digital signal. In exemplary embodiments, the analog-to-digital converter 316 is operably connected to a digital signal processor ("DSP") 317 for processing of the digital signal.

Converting the analog signal from the sensor 313 into a digital signal allows for the accurate separation of different magnitudes of acoustic response into "bins" corresponding to different glucose concentration levels, these "bins" being separated by pre-determined threshold values. For example, an acoustic response of a first magnitude or less could be determined to correlate to a glucose concentration level of about 100 mg/dl or below, which could be determined by the signal processor 320 as corresponding to a "hypoglycemic" glucose level. An acoustic response having a magnitude between the first magnitude and a second magnitude could be determined to correlate to a glucose concentration of between about 100 mg/dl and about 200 mg/dl, which could be determined by the signal processor 320 as corresponding to a "normal" glucose level. Still further, an acoustic response having a magnitude greater than the second magnitude could be determined to correlate to a glucose concentration of over about 200 mg/dl, which could be determined by the signal processor 320 as corresponding to a "hyperglycemic" glucose level.

As will later be explained in more detail with respect to FIG. 11, in an embodiment, upon determination of a "hypoglycemic" or "hyperglycemic" glucose level, the signal processor 320 is configured to transmit a warning signal to the user of the analyte monitor, or to take some other form of action (such as automatically activating an insulin pump).

Furthermore, by "binning" the acoustic responses using pre-determined thresholds, a more computationally efficient and accurate monitoring of glucose concentration level results. In particular, by comparing the magnitude of the acoustic response to pre-determined thresholds, hypoglycemic and hyperglycemic events may be detected more quickly and more accurately by the signal processor 320.

Figure 4:
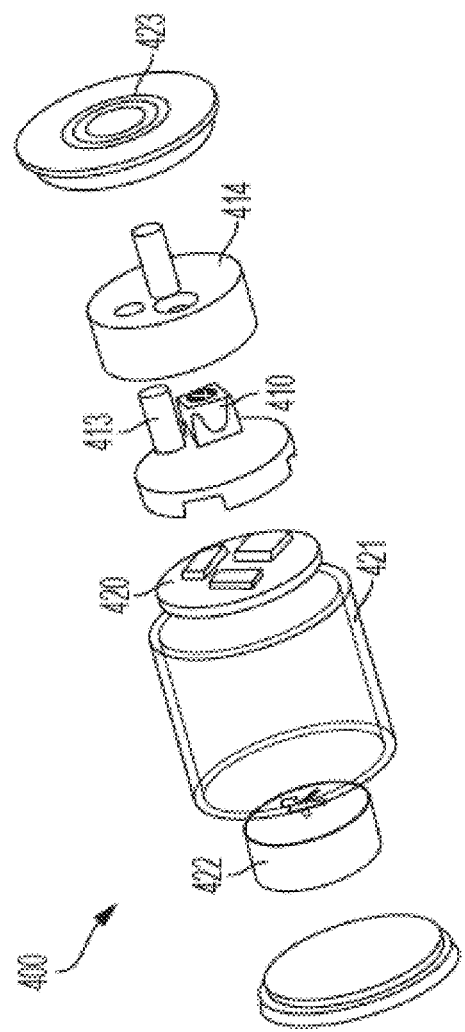
FIG. 4 shows an exploded view of an analyte monitor in accordance with exemplary embodiments.

Turning to FIG. 4, an exploded-view diagram of an analyte monitor 400 in accordance with an embodiment is shown. The analyte monitor 400 includes a light emitter 410 configured to emit light of a pre-determined wavelength. The analyte monitor 400 further includes a sensor 413 configured to detect acoustic waves generated from the volumetric expansion of an analyte of interest after irradiation of that analyte of interest with light generated by the light emitter 410. The analyte monitor 400 further includes a resonance chamber 414 sized and configured to form a standing wave from the acoustic waves so as to amplify the magnitude of the acoustic waves. The analyte monitor 400 further includes a signal processor 420 configured to estimate an analyte concentration level based on the magnitude of the sensed acoustic response.

In exemplary embodiments, the analyte monitor 400 further includes a power source 422 configured to supply power to one or more of the light emitter 410, the sensor 413 and the signal processor 420, or other components of the analyte monitor 400.

In exemplary embodiments, the analyte monitor 400 further includes a case 421 configured to surround one or more of the above-described components. In exemplary embodiments, the case 421 may comprise a case cover having a transmitter 423 incorporated into the case cover. In other exemplary embodiments, the transmitter 423 is located elsewhere in the analyte monitor, for example proximate to the signal processor 420. Incorporation of the transmitter 423 into the case cover allows for the transmitter 423 to have a larger size than if the transmitter 423 were to be located inside the case 421 of the analyte monitor 400 and also to reduce the overall size of the analyte monitor. For example, in instances where the transmitter 423 comprises an antenna (for example a RF antenna), the increased size of the transmitter 423 allows for a more powerful signal to be generated by the transmitter 423.

The transmitter 423 is operably connected to the signal processor 420. When a measured analyte concentration is determined to be outside of a "normal" range, the transmitter 423 is configured to transmit a signal responsive to this determination. For example, in an embodiment, the transmitter 423 is configured to transmit a signal to a remote device (not shown), such as a smartphone or smartwatch, in order to warn the user of the analyte device of the high or low analyte concentration level. Additionally or alternatively, the transmitter 423 is configured to transmit a signal to a remote device (not shown) for application of an additional substance to the user of the analyte monitoring device, such as an insulin pump for delivering insulin to the patient.

Figure 5:
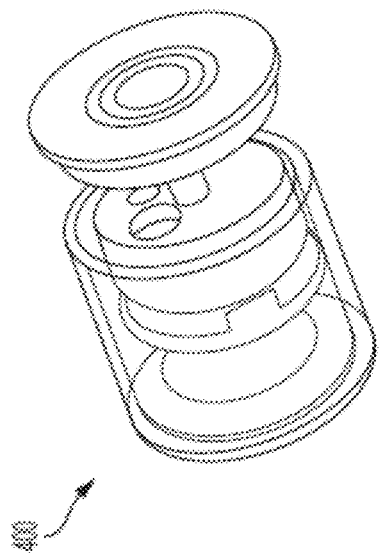
FIG. 5 shows an angled partially transparent perspective view of an analyte monitor in accordance with exemplary embodiments.

FIG. 5 shows an angled phantom view of a partially-assembled analyte monitor 400. As can be seen in FIG. 5, the assembled analyte monitor 400 may have a length of around below about 50 mm, for example below about 40 mm, such as below about 30 mm, preferably below about 20 mm, most preferably about 15 mm. The assembled analyte monitor 400 may have a width of below about 50 mm, for example below about 40 mm, such as below about 30 mm, preferably below about 20 mm, most preferably about 18 mm. As such, the assembled analyte monitor 400 may be worn discretely by a user, or even incorporated into jewelry or clothing of the user, for example incorporated into an earring, a watch or a bracelet.

Figure 6:
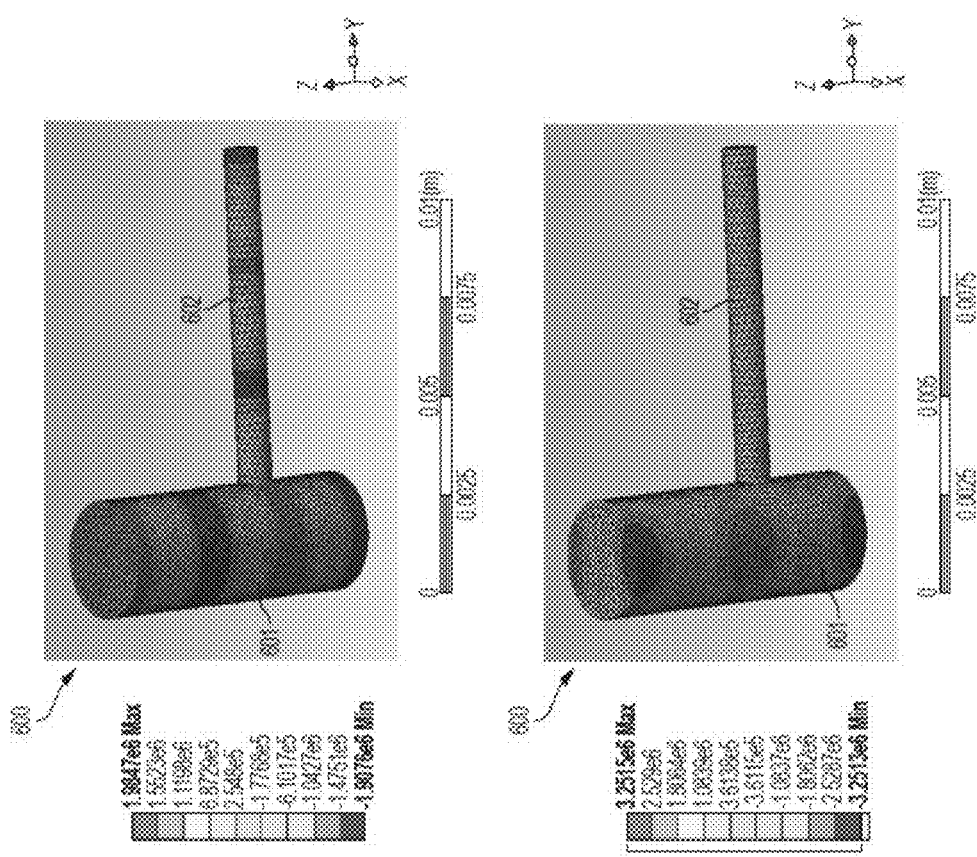
FIG. 6 shows computer simulations of a resonance chamber in accordance with exemplary embodiments.

Another view of a resonance chamber in accordance with exemplary embodiments is shown in FIG. 6. In FIG. 6, two computer models of a resonance chamber 600 are shown. The resonance chamber 600 includes a resonance branch 601 and a measurement branch 602. The resonance branch 601 is sized and dimensioned so as to form a standing wave, in the manner as described above. The measurement branch 602 connects the resonance branch 601 to the sensor.

As can be seen in the two figures of FIG. 6, the length of the resonance branch 601 and the placement of the measurement branch 602 along the resonance branch are important for obtaining a clear signal of the acoustic response. In particular, as can be seen in the bottom figure of FIG. 6, the measurement branch 602 is positioned adjacent to a node of the standing wave formed in the resonance branch 601. As such, minimal propagation of the acoustic wave down the measurement branch 602 occurs, and a lower magnitude acoustic response is measured by the sensor. Further, as can be seen in the top figure of FIG. 6, the measurement branch 602 is positioned close to an antinode of the standing wave formed in the resonance branch 601. As such, a good propagation of the acoustic wave down the measurement branch 602 occurs, and an acceptable magnitude acoustic response signal is measured by the sensor. As such, in an exemplary embodiment, the measurement branch 602 is positioned proximate to an anti-node of the standing wave to be formed in the resonance chamber 600.

When developing the analyte monitor described above, the inventors recognized that the acoustic responses of each user to the light emitted from the light emitter are individual. In other words, a variety of variables may affect the acoustic response of a user, such as skin transmittivity, skin composition, sweat gland activity and so on. As such, the inventors found that a training procedure to personalize the analyte monitor to an individual user increased the accuracy of the analyte monitor in detecting raised or lowered analyte concentrations.

Figure 7:
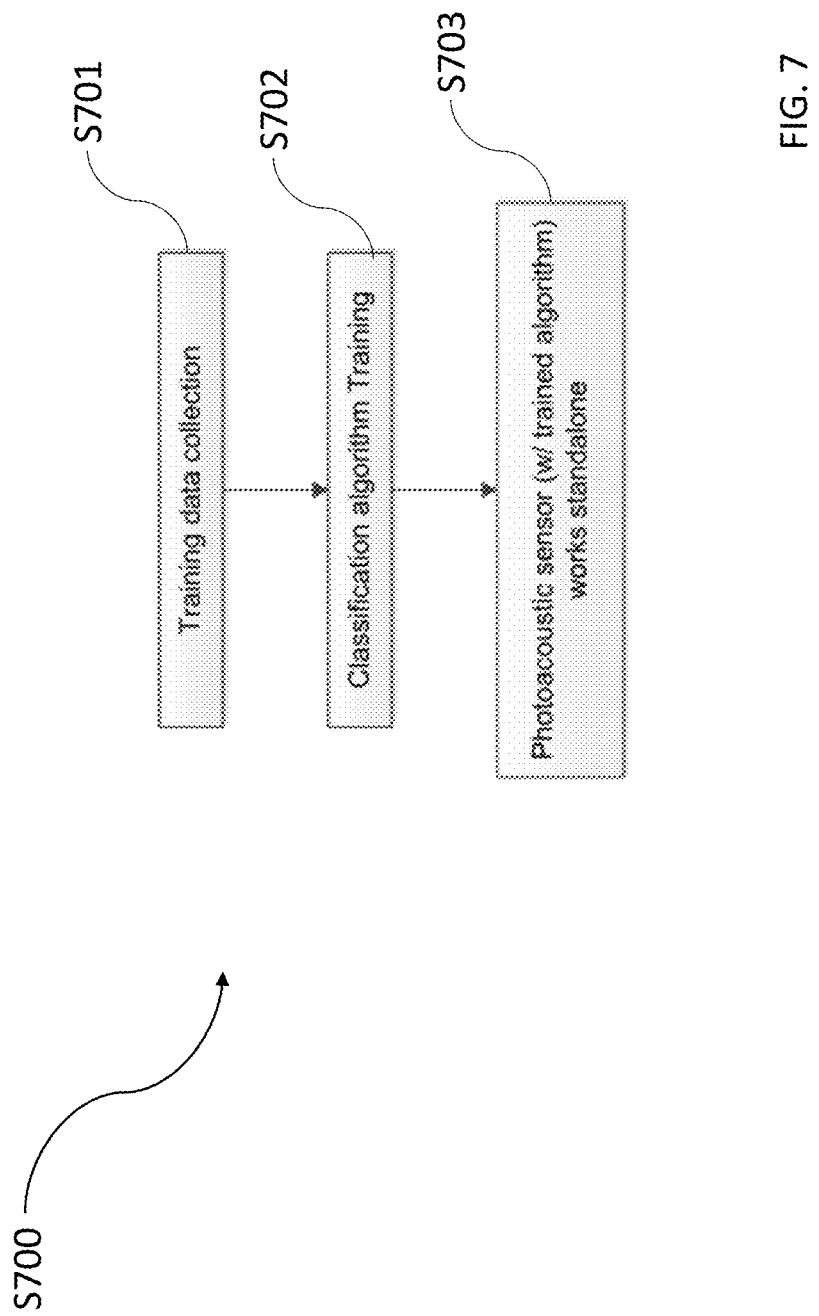
FIG. 7 shows a flowchart of a method in accordance with exemplary embodiments.

FIG. 7 shows an overview of a general method S700 for training an analyte monitor for a specific user. The individual steps of this general method will be explained in more detail with reference to FIGS. 8, 9, 10 and 11. At step S701, training data for training a signal processor of the analyte monitor is collected from a specific user. In an embodiment, the training data is collected by obtaining analyte concentration levels of the user from a conventional analyte monitor, such as a commercially-available continuous glucose monitor having an invasive component (such as a transdermal probe), in combination with measuring acoustic responses from the analyte monitor in accordance with various embodiments as described herein. After sufficient training data has been collected from the user, the method progresses to step S702.

At step S702, the algorithm used by the signal processor to correlate certain acoustic signal responses to the obtained analyte concentration levels is trained using the training data collected from the user. In an embodiment, the training of the signal processor is a supervised machine learning process, where training data is first labelled and then used in training. In an embodiment, after the signal processor is trained using the training data, the signal processor may be tested against validation data to determine the accuracy of the signal processor in determining analyte concentration levels. After training of the signal processor to an acceptable accuracy, the method progresses to step S703.

At step S703, the analyte monitor has been adapted to the individual characteristics of the user and is used to monitor an analyte concentration level of the use without the concurrent use of another analyte monitor.

Each of the steps S701, S702 and S703 of the method S700 will now be described in more detail.

Figure 8:
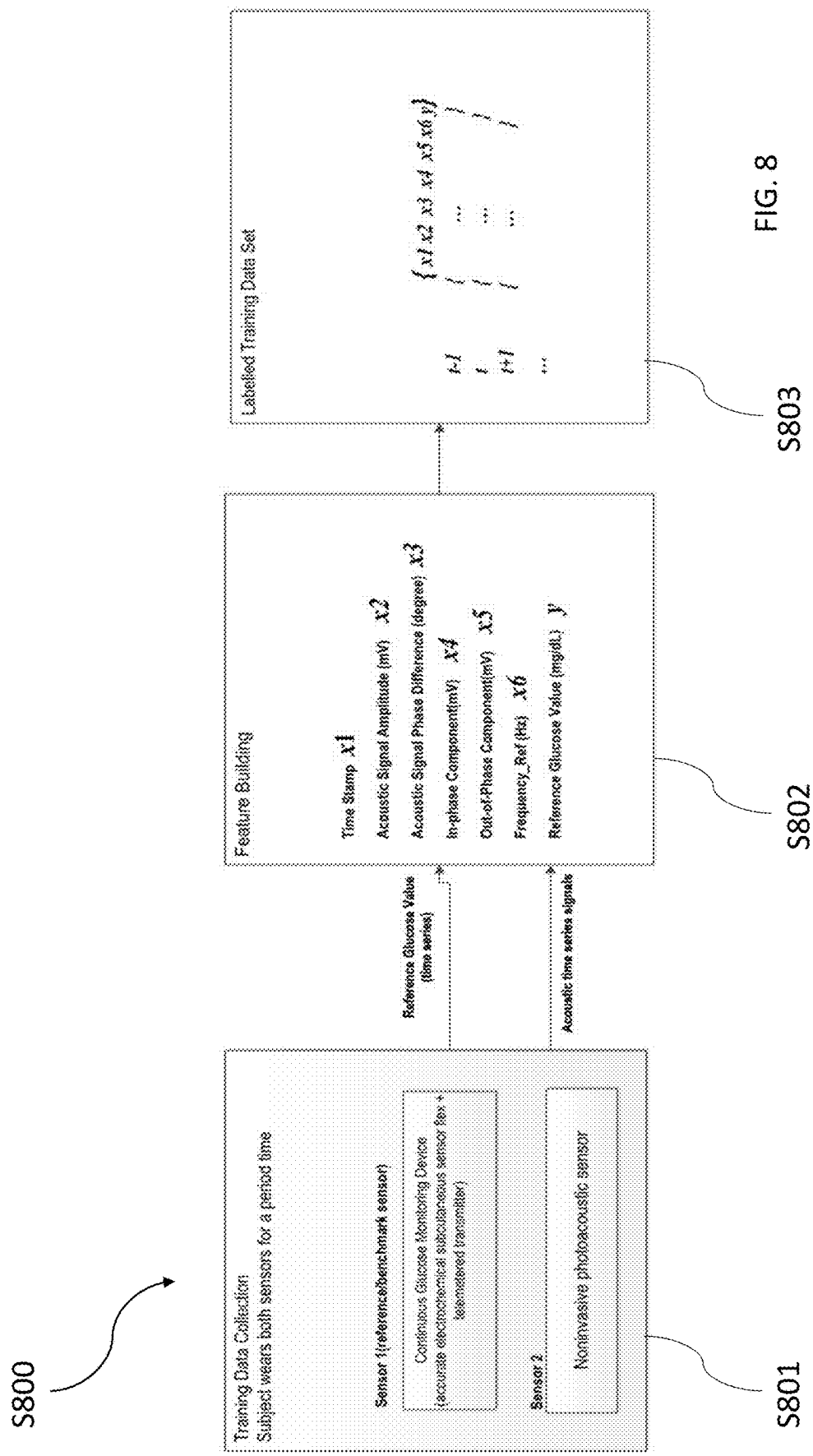
FIG. 8 shows a flowchart of another method in accordance with exemplary embodiments.

FIG. 8 shows a more detailed flowchart S800 illustrating exemplary steps involved in the collection of a training data set of step S701. At Step S801, data is collected from a specific user via two or more analyte monitors. One of these analyte monitors is an analyte monitor in accordance with exemplary embodiments as described herein, and at least one other of these analyte monitors comprises a conventional analyte monitor, such as a continuous glucose monitor comprising a transdermal probe. The conventional analyte monitor collects data related to the user's blood analyte concentration levels to be used as reference data. The analyte monitor in accordance with various embodiments obtains acoustic responses in parallel with obtaining the reference data.

As the reference data is obtained in parallel with the acoustic responses, it is possible to correlate features of the acoustic responses to the reference data. In Step S802, features (x1, x2, x3, x4, x5 and x6) of the acoustic response signals detected by the sensor of the analyte monitor in accordance with exemplary embodiments are associated with the simultaneously-obtained analyte reference values (y) obtained by the conventional analyte monitor.

For example, if the analyte of interest is glucose, reference glucose concentration values (y) obtained from the conventional analyte sensor can be associated with the time stamp (x1), amplitude (x2), phase difference (x3), in-phase component (x4), out-of-phase component (x5) and frequency (x6) of the acoustic signal response obtained via the analyte monitor in accordance with exemplary embodiments. It is to be noted that the above list of features is not an exhaustive list, and other features of the acoustic signal response may additionally or alternatively be associated with the reference glucose concentration values (y) obtained from the conventional analyte monitor.

After association of the features (x1, x2, x3, x4, x5 and x6) of the acoustic response to the reference data (y), the method progresses to step S803, where a labelled training data set is constructed, using conventional techniques, with this data.

Figure 9:
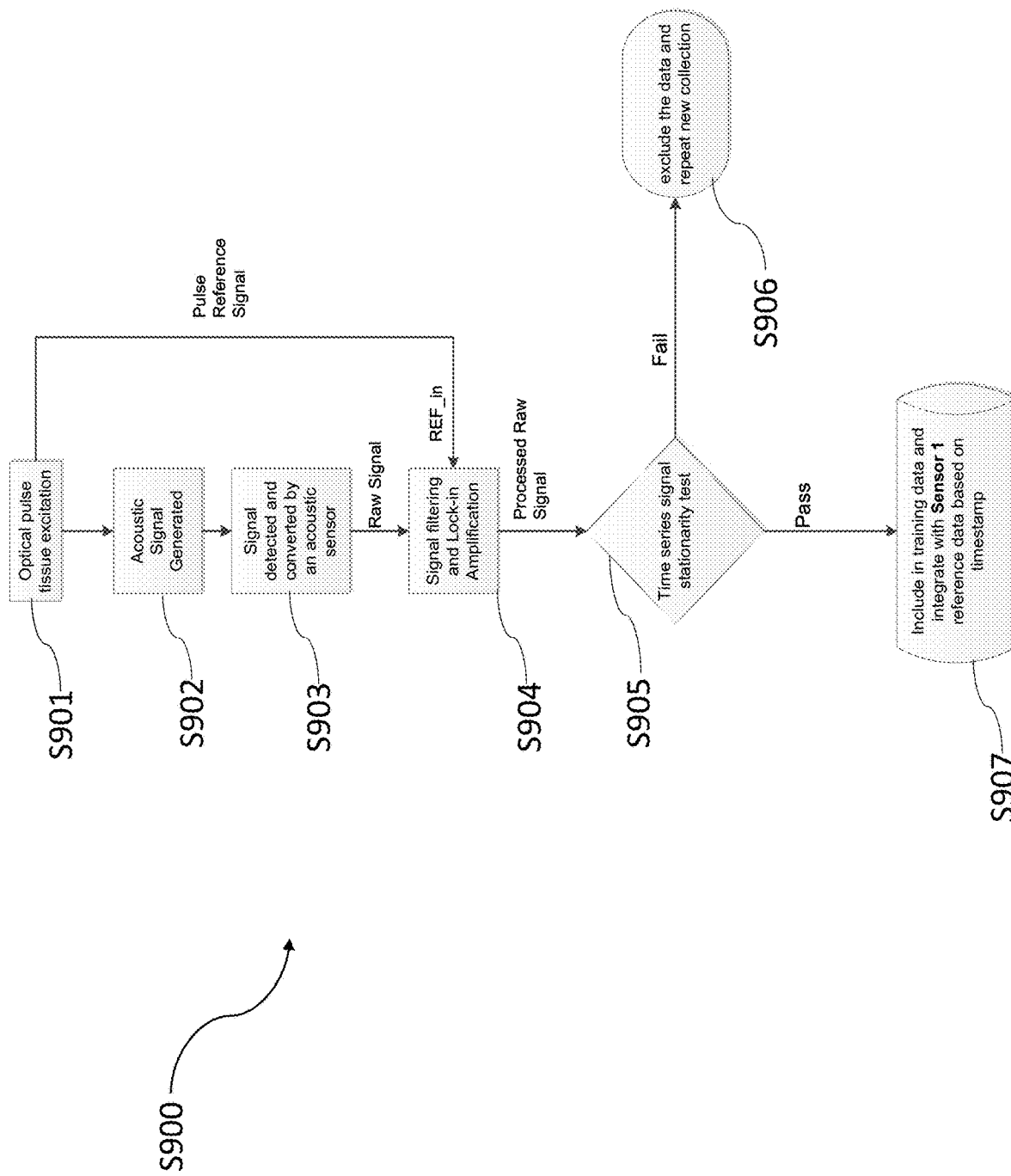
FIG. 9 shows a flowchart of another method in accordance with exemplary embodiments.

In FIG. 9, a further flowchart S900 shows how training data is collected by the analyte monitor in accordance with exemplary embodiments as described herein. At Step S901, tissue of a user is excited via an optical pulse from a light emitter. The method then progresses to step S902.

At Step S902, an acoustic signal is generated by analytes in the tissue in response to the optical pulse.

At Step S903, this acoustic signal is detected by a sensor and converted into an electrical signal, in the same manner as described previously.

At Step S904, the electrical signal is filtered to reduce the amount of noise in the signal. In an embodiment, this filtering is achieved through the use of a bandwidth filter. In an embodiment, this filtering is achieved via a time-based filtering technique, where a pulse reference signal generated at the same time as the emission of the optical pulse in Step S901, and wherein only acoustic signals received a predetermined time after the pulse reference signal has been generated are allowed through the signal filter. Additionally or alternatively, this signal filtering may utilize timestamps associated with the pulse frequency of light to filter out noise through a comparison of the timestamps of the emitted light and the timestamps of acoustic signal responses to the light. Also at Step S904, the filtered electrical signal is amplified, for example through the use of an operational amplifier. The method then progresses to Step S905.

At Step S905, a time series stationarity test is applied to the filtered, amplified electrical signal in order to test for noise in the signal caused by, for example, contact pressure and/or motion of the user. If the signal fails this time series stationarity test, the method progresses to Step S906, where the collected data is excluded from the training data set. If the signal passes this time series stationarity test, the method progresses to Step S907, where the collected data is included in the training data set for training the analyte monitor according to various embodiments as described herein.

The method S900 is repeated until sufficient data has been collected to form a training data set large enough for training the algorithm used by the signal processor.

Figure 10:
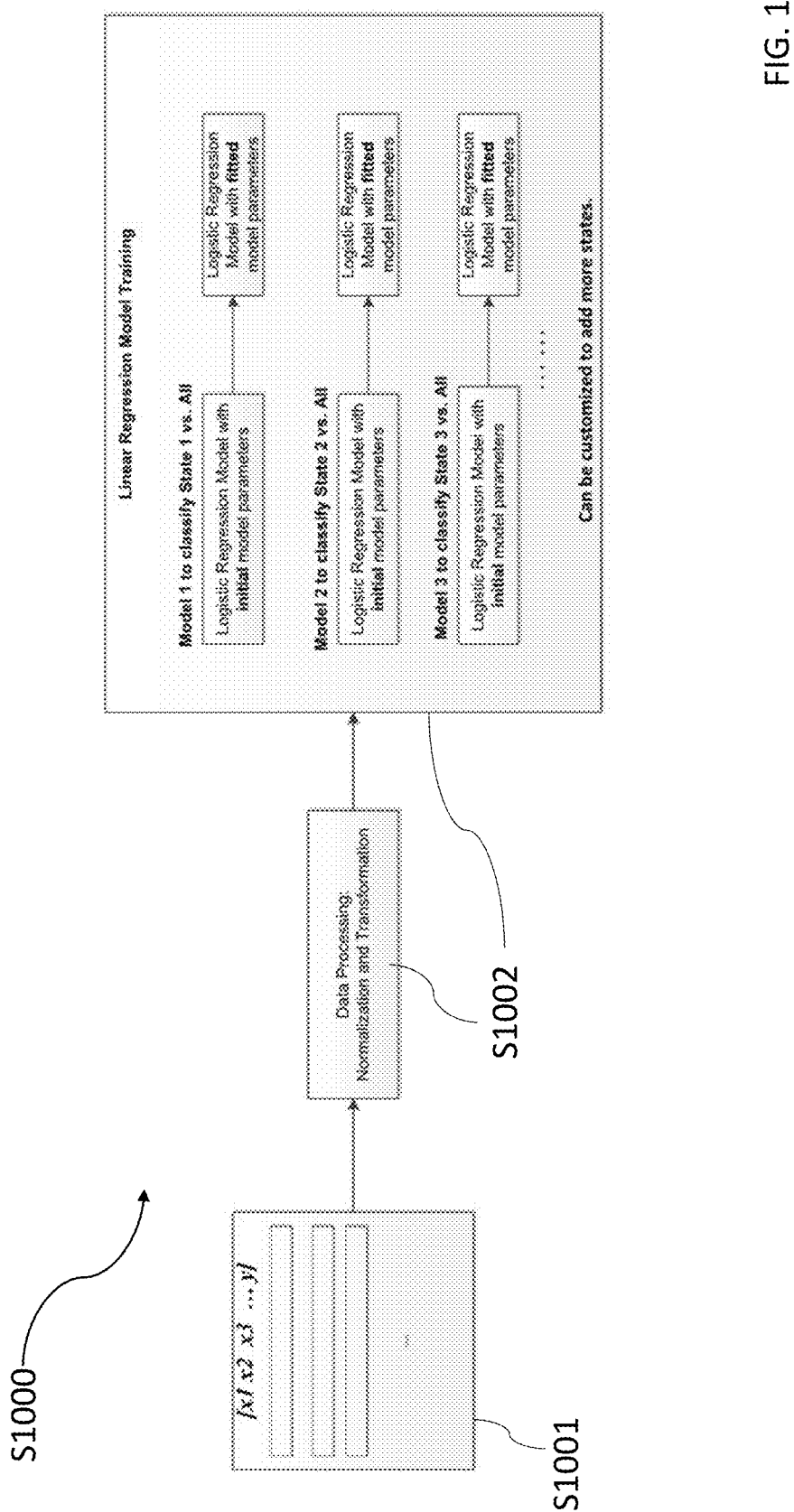
FIG. 10 shows a flowchart of another method in accordance with exemplary embodiments.

FIG. 10 shows a detailed flowchart S1000 illustrating exemplary steps involved in the training of the algorithm used in the digital signal processor as per step S702 in method S700. At Step S1001, the labelled training data set is completed. The method then progresses to Step S1002.

At Step S1002, a supervised learning method is used to train the algorithm used by the digital signal processor on the labelled training data set. More specifically, the algorithm used by the digital signal processor uses the features (x1), (x2), (x3), (x4), (x5) and (x6) of the electric signal derived from received acoustic responses and estimates a glucose concentration level based on these features. The estimated glucose concentration level is then compared to the obtained glucose concentration level (y) corresponding to those features as obtained from the conventional analyte monitor. Based on the accuracy of the comparison, parameters of the algorithm are adjusted. Statistical normalization and transformation techniques, such as linear regression techniques, may be used in this adjusting of parameters.

After the parameters have been adjusted, the glucose concentration level is again estimated and compared to the obtained glucose concentration level (y) corresponding to those features as obtained from the conventional analyte monitor. In this manner, the algorithm is iteratively trained to more accurately estimate the glucose concentration level of the user based on the features of the acoustic response signal obtained from the analyte monitor in accordance with various embodiments. When the algorithm is fully trained, a more accurate personalized calibration for a specific user is achieved. In particular, the analyte monitor according to embodiments as described herein is better able to account for variations in the skin conditions and characteristics of a specific user.

Figure 11:
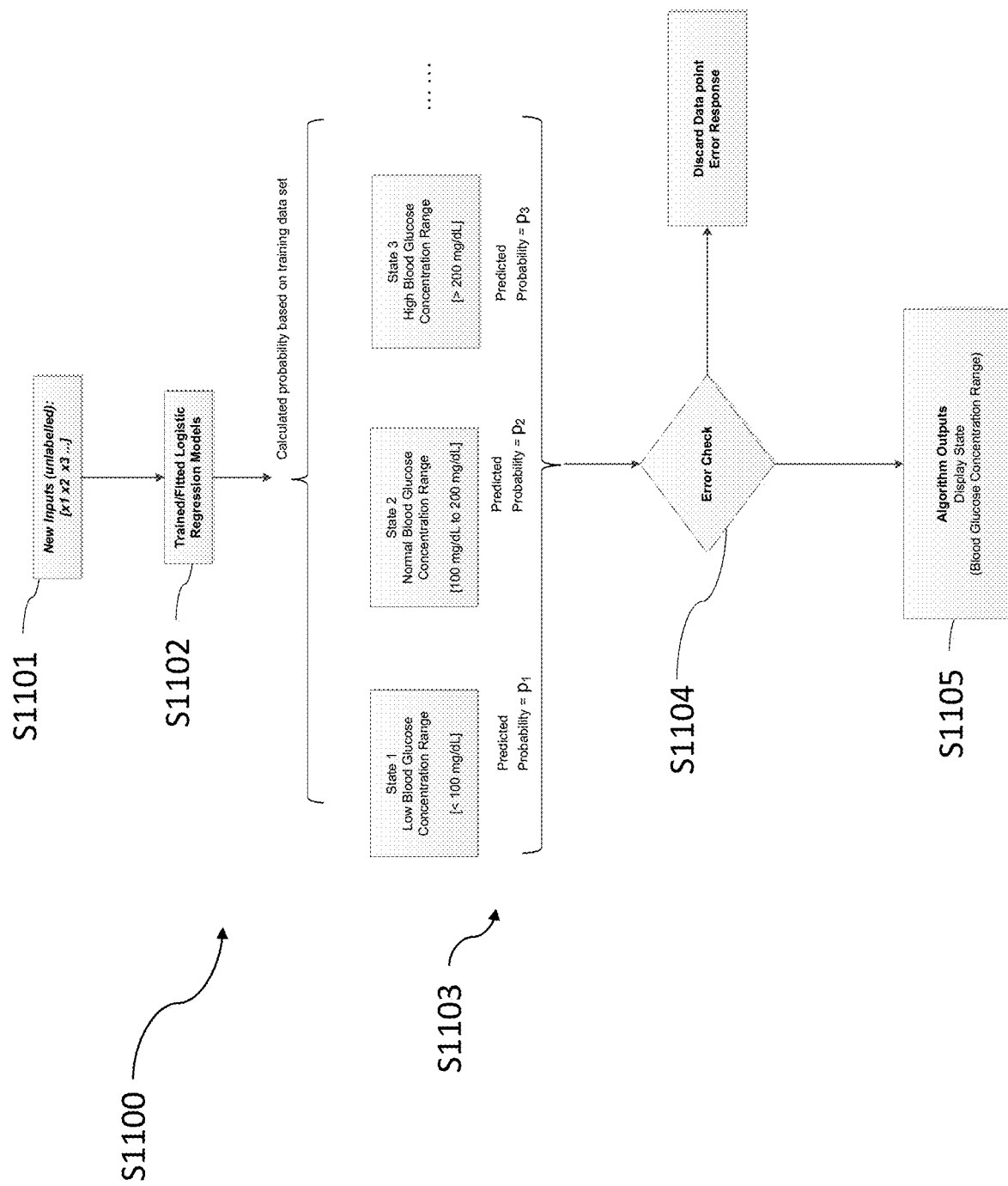
FIG. 11 shows a flowchart of another method in accordance with exemplary embodiments.

FIG. 11 shows a more detailed flowchart S1100 of the use of a trained analyte monitor in monitoring analyte concentration levels of a user, as per step S703 in FIG. 7.

At step S1101, the trained analyte monitor obtains acoustic responses that are converted into electrical signals having features (x1, x2, x3, etc.) that can be used to estimate an analyte concentration of a user. The method then progresses to step S1102.

At Step S1102, the features of the electrical signal are used, using the algorithms of the trained digital signal processor module, to estimate an analyte concentration level. After estimation of the analyte concentration level, the method progresses to step S1103.

At Step S1103, the estimated analyte concentration level is sorted into a "bin", each bin corresponding to analyte concentration levels of a particular user state. For example, the estimated analyte concentration level is a blood glucose concentration level, and the estimated glucose concentration level is sorted into one of three bins, the first bin having a range of below about 100 mg/dl and corresponding to a hypoglycemic state, the second bin having a range of between about 100 mg/dl and 200 mg/dl and corresponding to a "normal" state, and the third bin having a range of above about 200 mg/dl and corresponding to a hyperglycemic state. In an exemplary embodiment, the end-points of the ranges of the bins are variable and can be varied on the basis of a particular user's blood glucose characteristics.

In an exemplary embodiment, a probability of the estimated blood glucose level falling within a certain bin is estimated by the trained algorithm of the digital signal processor, based on the features of the electrical signal derived from the acoustic response. In this manner, a probabilistic confidence level of the "binning" step can be determined. In exemplary embodiments, multiple estimations of the blood glucose level can be performed, and the confidence level can be iteratively re-evaluated on the basis of each subsequent estimation. In this manner, a high confidence level of the binning of the blood glucose concentration estimation can be achieved.

After the analyte concentration estimation is binned, the method progresses to Step S1104. At step S1104, the algorithm of the digital signal processor outputs the "state" corresponding to the estimated analyte concentration level. For example, if the estimated blood glucose concentration level was above 200 mg/dl, the algorithm would output a "hyperglycemic" state. After outputting of this state, the method progresses to Step S1105.

At Step S1105, action is performed in response to the output of the state, if required. For example, if a "hyperglycemic" state is output by the analyte monitor, an alert may be transmitted to a remote device so as to warn the user of this state. Additionally or alternatively, a signal may be transmitted to an insulin pump so as to administer an amount of insulin in response to the output of the state. Additionally or alternatively, a signal is transmitted to a display device to display the blood glucose concentration state.

Figure 12:
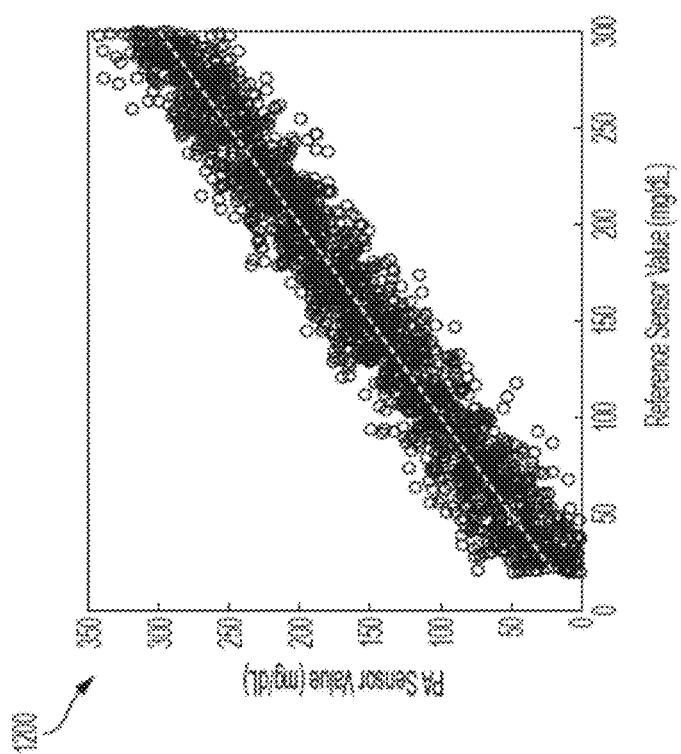
FIG. 12 shows a graph comparing results obtained from an analyte monitor in accordance with exemplary embodiments to a conventional analyte monitor.

In order to test the accuracy of glucose concentrations estimated with the analyte monitor of embodiments as described herein and a conventional continuous glucose monitor having a transdermal probe, glucose concentration measurements were tested simultaneously in-silico using a trained analyte monitor according to an embodiment and a transdermal continuous glucose monitor and then compared to each other. The results of these comparisons are shown in the graph 1200 of FIG. 12. As shown in FIG. 12, the glucose concentrations estimated by the trained analyte monitor in accordance with embodiments as described herein closely matched the glucose concentrations measured using a conventional, commercially-available continuous glucose monitor having a transdermal probe.

Glucose concentration estimations were also obtained with an in-silico simulation of untrained analyte monitor in accordance with embodiments as described herein and compared to the glucose concentrations estimations obtained with a trained algorithm prototype analyte monitor in accordance with embodiments as described herein. It was determined that the prototype untrained analyte monitor had a success rate of about 60% in determining hypoglycemic events, whereas the prototype trained analyte monitor had a success rate in excess of about 85% in determining hypoglycemic events, thereby demonstrating the effect of the machine learning training algorithm in improving the accuracy of glucose concentration estimations.

Figure 13:
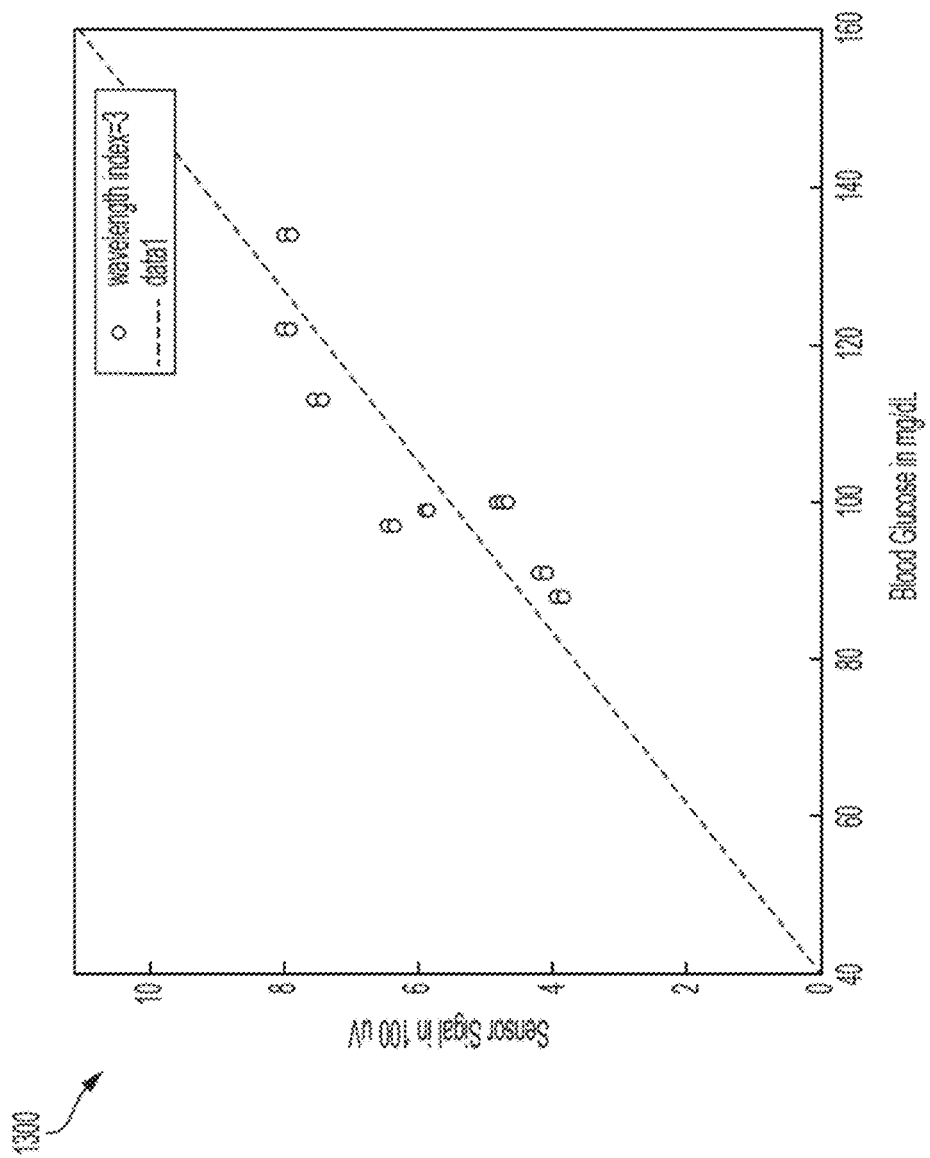
FIG. 13 shows another graph comparing results obtained from an analyte monitor in accordance with exemplary embodiments to a conventional analyte monitor.

Further, in-vivo, experiments were also performed, as shown in the graph 1300 of FIG. 13. As can be seen in FIG. 13, there is a strong correlation between the sensor signal obtained from the analyte monitor in accordance with embodiments having a trained algorithm and a known blood glucose concentration level obtained from a reference sensor, thereby indicating the accuracy of this method in detecting blood glucose concentration levels.

The various tasks performed in connection with the processes described herein may be performed by software, hardware, firmware, or any combination thereof. For illustrative purposes, the following description of process S700 may refer to elements mentioned in connection with FIGS. 1 to 6. In practice, portions of process S700 may be performed by different elements of the described system, e.g., the digital signal processor module or a different controller module. It should be appreciated that process S700 may include any number of additional or alternative tasks, the tasks shown in FIG. 7 need not be performed in the illustrated order, and process S700 may be incorporated into a more comprehensive procedure or process having additional functionality not described in detail herein. Moreover, one or more of the tasks shown in FIG. 7 could be omitted from an embodiment of the process S700 as long as the intended overall functionality remains intact.

Calibration Techniques

It will be appreciated that tissue properties (such as skin water content, fibrotic and so on) will differ from user to user. It will additionally be appreciated that skin properties of an individual user may change over a given time period.

Variations in tissue skin properties give rise to a resultant variation in the acoustic signal response caused by the thermal excitation of the analyte molecules targeted by the emitted light. This variation in the acoustic signal response may be independent on the concentration level of the analyte itself (e.g., glucose level or diabetic ketoacidosis). As such, this variation in acoustic signal response may result in an inaccurate determination of the concentration of the analyte via the methods and systems described above.

In order to compensate for this variation in the acoustic signal response, the analyte monitor according to embodiments of the present invention may be calibrated on the basis of additional techniques, as will be explained in more detail below.

Electrical Impedance Spectroscopy (EIS)

Electrical Impedance Spectroscopy is a technique for monitoring analyte concentrations in a target, such as glucose concentrations. In this technique, a voltage is applied to a target using electrodes. The target's current response is then measured. The knowledge of the characteristics of the applied voltage and the consequent current response allows for an impedance of the tissue to be calculated, which impedance includes both a real component (corresponding to the target's resistance) and an imaginary component (corresponding to the target's reactance).

An analyte concentration level may be determined using EIS based on the measurement of the target impedance itself. However, in the methods described herein, EIS is not itself used to determine the analyte concentration directly. Instead, in the methods described herein, EIS is used to determine an impedance level of the target that will subsequently be used to detect variation in the acoustic response caused by changes to the target that are not associated with varying analyte concentration levels.

Using the example of the target being tissue of a user and the analyte of interest being glucose, it may be determined that an increasing water content in the skin of the user causes a decrease in the acoustic signal response. It may also be determined that an increasing water content in the skin of the user may result in a larger reactance component of the impedance determined by EIS, since a higher water content typically results in a higher skin capacitance. It may also be determined that a change in target pH level causes an increase or decrease in the acoustic signal response.

For the above example, measuring the skin impedance using EIS concurrently with measuring the acoustic signal obtained from the photoacoustic techniques detailed above allows for a determination that a smaller acoustic response is not the result of a decrease in glucose concentration (which may in some circumstances require some additional action to be taken, such as prompting the user to raise their glucose concentration levels) but is instead the result of an increase in skin water content.

In this manner, the use of EIS may increase the accuracy of the analyte monitor described above.

Figure 14:
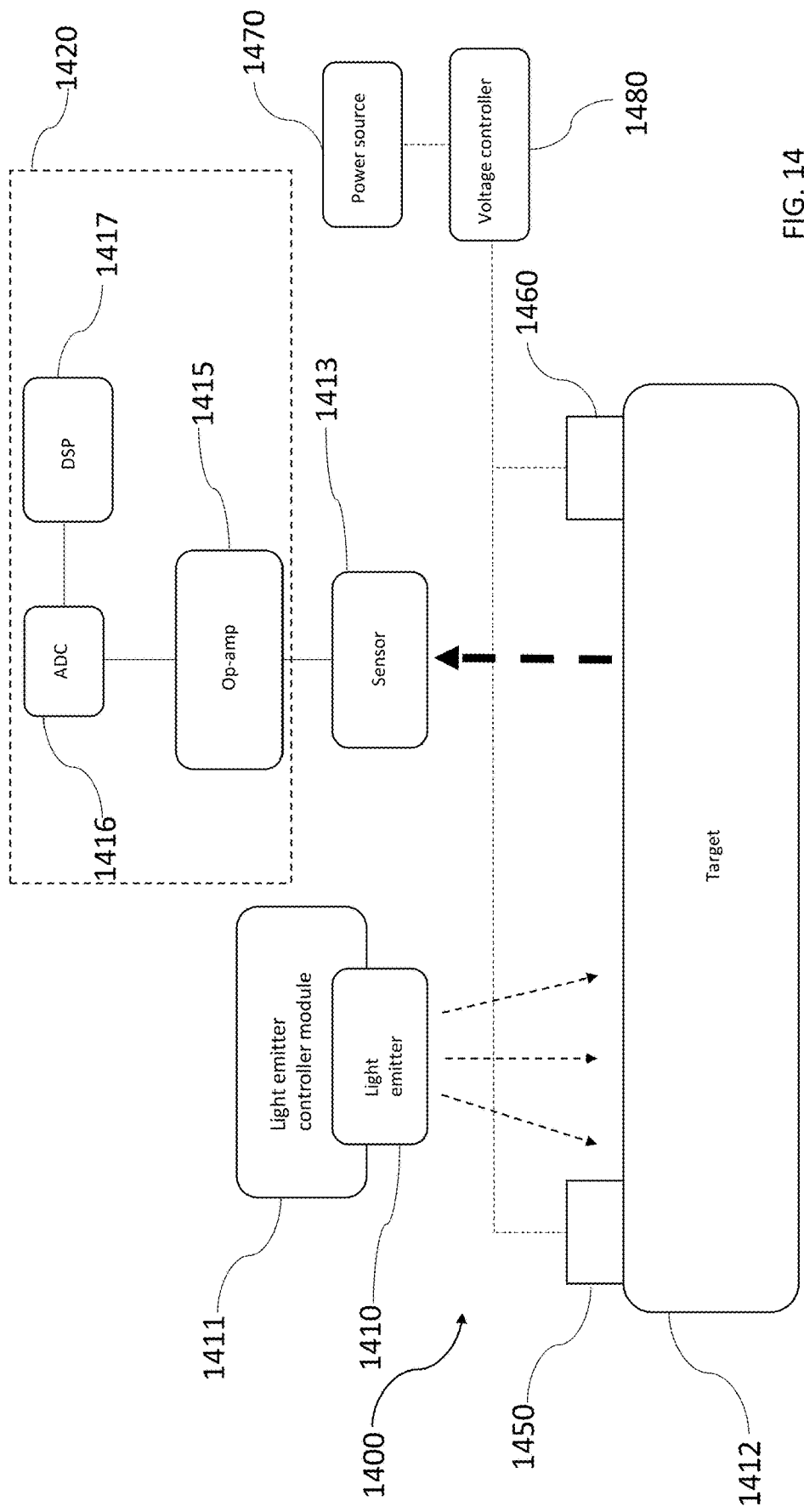
FIG. 14 shows a schematic of an analyte monitor in accordance with exemplary embodiments.

FIG. 14 shows a logical schematic illustrating an analyte monitor including additional elements for implementing EIS calibration. As can be seen in FIG. 14, the analyte monitor 1400 includes a light emitter 1410 for emitting light (shown with thin dashed lines) towards a target 1412. In an exemplary embodiment, the light emitter 1410 comprises a light-emitting diode (LED). In some embodiments, the light emitter 1410 comprises a laser chip. A light emitter controller module 1411 includes circuitry associated with the light emitter 1410. In exemplary embodiments, the light emitter controller module 1411 is configured to control the light emitter 1410 such that the pulses of light emitted by the light emitter 1410 have a pre-determined or a variable pulse repetition frequency (PRF). In other words, the light emitter controller module 1411 is suitable for modulating the frequency of the light pulses emitted by the light emitter 1410. Preferably, the light emitter controller module 1411 is configured to control the light emitter 1410 so as to emit light pulses having a duration of about 500 ns per pulse at a frequency of about 50 kHz or more. This pulse duration and frequency has been found to achieve a good acoustic response for certain analytes of interest, such as glucose.

The analyte monitor 1400 further includes a sensor 1413, for example a microphone or a transducer, such as a piezoelectric transducer. The sensor 1413 is configured to detect acoustic waves (shown with a bold dashed line) emitted from the thermal excitation of analyte molecules and volumetric expansion in the target 1412 by the light emitted from the light emitter 1410 and generate an electrical signal based on these acoustic waves.

In exemplary embodiments, the sensor 1413 is operably connected to a signal processor 1420. In the embodiment shown in FIG. 14, the signal processor 1420 includes an operational amplifier ("op-amp") 1415 configured to further amplify the electronic signal derived from the acoustic response of the target 1412. In exemplary embodiments, the op-amp 1415 is operably connected to an analog-to-digital converter 1416 configured to convert the analog electrical signal from the sensor 1413 to a digital signal. In exemplary embodiments, the analog-to-digital converter 1416 is operably connected to a digital signal processor ("DSP") 1417 for processing of the digital signal. It will be appreciated that the above-described components 1410, 1411, 1413 and 1420 of the analyte monitor 1400 may be contained within a singular housing or may be contained separately within different housings.

In exemplary embodiments, the op-amp 1415 is adjustable so as to adjust the gain or amplification amount of the op-amp. In this manner, the amplification of the electronic signal derived from the acoustic response of the target 1412 may be adjusted as desired so as to ensure that this electronic signal is large enough to be accurately measured without causing saturation of this electronic signal.

The analyte monitor further includes a first electrode 1450 and a second electrode 1460. The first and second electrodes 1450, 1460 are operably connected to a power source 1470 and a voltage controller 1480. The power source 1470 and the voltage controller 1480 are together configured to supply a voltage to the first and second electrodes 1450, 1460. In exemplary embodiments, this voltage has the form of an alternating voltage. In exemplary embodiment, the peak-to-peak voltage of the applied alternating voltage is between around 0.1V to around 2V, preferably from around 0.2V to around 1.5V. The frequency of the alternating current may be from around 0.5 kHz to around 3 kHz, preferably from around 1 kHz to around 2 kHz. The first and second electrodes 1450, 1460 may be spaced from one another by a distance of from around 0.1 µm to around 5 cm, preferably from around 0.5 µm to around 4 cm.

In use, the current response of the target to the applied alternating voltage is measured in order to determine the impedance of the target. The impedance measurement is then used to determine if a reduction in the strength of the acoustic response from the thermal excitation of analyte molecules is not due to a decrease in the concentration of analyte molecules but is instead due to some other characteristic of the target changing, such as the water content of the target changing.

In some embodiments, in order to correctly correlate a particular measured impedance value to a particular characteristic of the target, a training period is implemented to correlate impedance measurements to expected skin characteristic variations of the target. During this training period, the analyte monitor is installed non-invasively on the target (e.g., on the outside of the user's skin) and impedance measurements are obtained over a period of several hours or days and monitored for trends together with photoacoustic methods. In the non-invasive installation of the analyte monitor on the target, the electrodes 1450, 1460 may be placed in direct or indirect contact with a surface of the target. Over this time period, it may be determined that the measured impedance may vary in a particular manner when skin water content is known to increase or decrease. For example, using the example of the target being a user's skin, it may be determined that the measured reactance of the user's skin decreases overnight, when the skin's water content is expected to decrease. Over this time period, a set of impedance measurements and photoacoustic measurements is obtained together with target data from another technique of obtaining analyte concentration values (such as a transdermal continuous glucose monitor or via fingerprick testing). This set of measurements is divided into a calibration data set and a validation data set. The calibration data set is then analyzed using a processor module in order to fit a model to this calibration data set. After the model is fitted, the model is run with only the impedance measurements and the photoacoustic measurements of the validation data set. The results of this run are compared to the target data obtained by the different technique in the validation data set. In this manner, the model can be trained to accurately predict analyte concentration values on the basis of both acoustic signal responses and impedance measurements.

Figure 15:
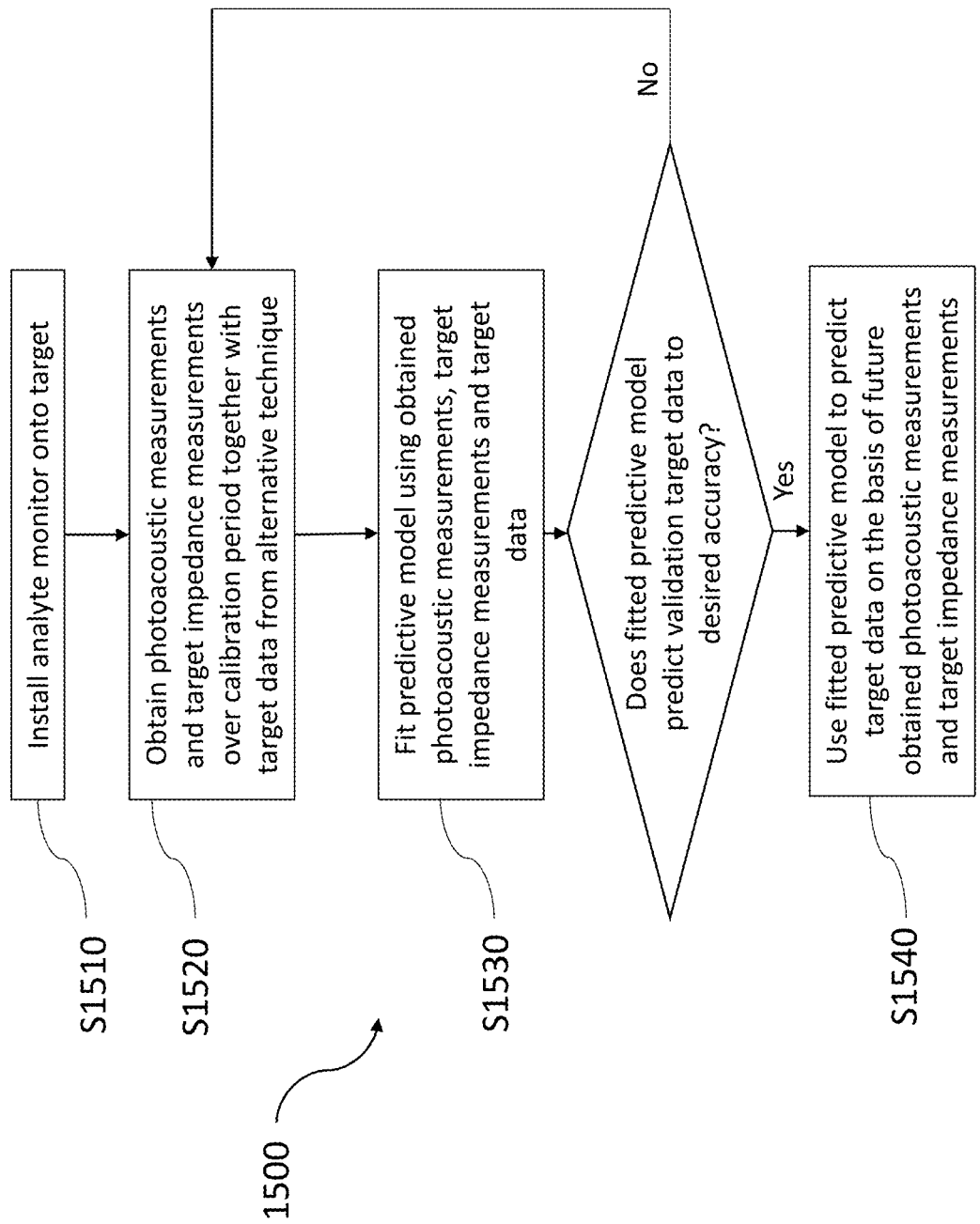
FIG. 15 shows a flowchart of a method of fitting a predictive model in accordance with exemplary embodiments.

FIG. 15 shows a method 1500 for training an analyte monitor including a photoacoustic sensor and electrodes for measuring target impedance via EIS. It is to be noted that the method 1500 is a particular implementation of the methods shown in FIGS. 7 to 11, with the measured impedance being a feature "$x_n$" that is taken into account with the other features described with respect to this method.

The method starts at step S1510. At step S1510 the analyte monitor is installed onto a target, for example a user. The method then progresses to step S1520. At step S1520, photoacoustic measurements and target impedance measurements are obtained over an initial calibration period together with another technique for obtaining analyte concentration values over this same period, such as a transdermal continuous glucose monitor (CGM) or "fingerprick" technique. These measurements are split into a training dataset and a validation dataset. After obtaining photoacoustic measurements, target impedance measurements and analyte concentration measurements, the method progresses to step S1530. At step S1530 a predictive model is fit using the training dataset (e.g., as described above with reference to FIGS. 7 to 11). In particular, the photoacoustic measurements and target impedance measurements may be used as input vectors of the training dataset, and the analyte concentration measurements may be used as a series of targets of the training dataset. The predictive model assigns various weights to the input vectors so as to better fit the predictive model using conventional techniques such as variable selection and parameter estimation. After the predictive model has been fitted, the method moves onto step 1540.

At step S1540, the fitted predicted model is used to predict target data on the basis of the photoacoustic measurements and the impedance measurements of the validation dataset. These predicted targets are then compared to the analyte concentration values of the validation dataset. If the fitted predictive model predicts the targets within a pre-determined accuracy threshold, the method progresses to step S1540. If the fitted predictive model does not predict the targets within a pre-determined accuracy, the method reverts to step S1510 for additional training and fitting.

At step S1540, the analyte monitor is fitted and predicts analyte concentration values on the basis of future-obtained photoacoustic measurements and target impedance measurements. There is no longer a need for an invasive technique for measuring analyte concentration levels.

Figure 16:
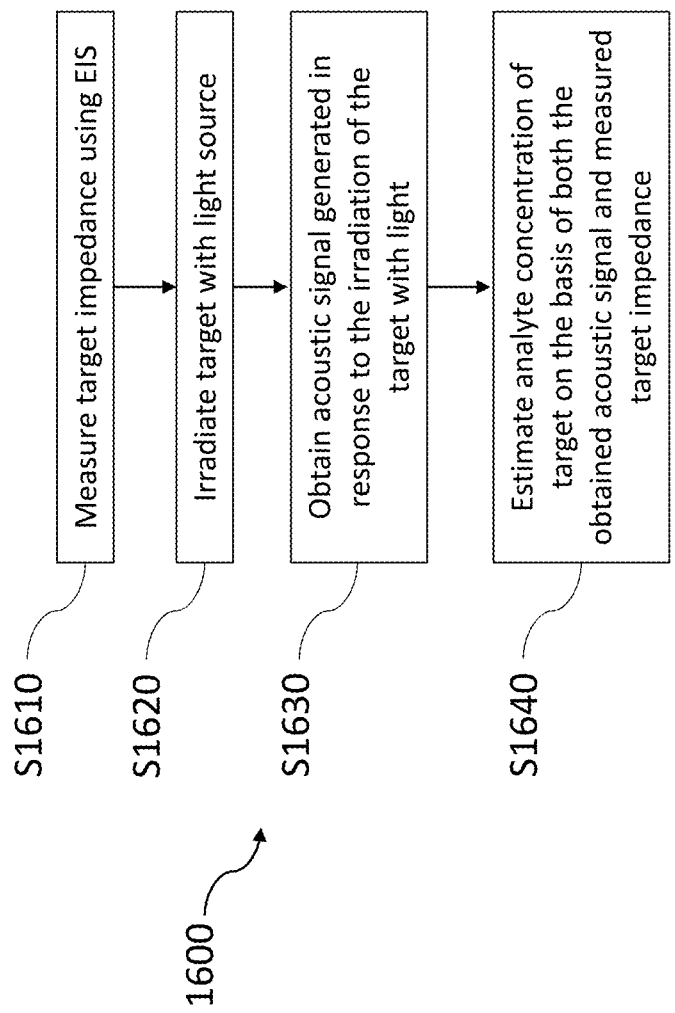
FIG. 16 shows a flowchart of a method in accordance with exemplary embodiments.

FIG. 16 shows a method 1600 for estimating analyte concentration levels in a target using an analyte monitor of the form as detailed above. The method begins at step S1610. At step S1610, an impedance of a target is measured using electrical impedance spectroscopy (EIS). The method then progresses to step S1620. At step S1620, the target is irradiated with light of a first wavelength from a light emitter. Preferably, the light of the first wavelength has a wavenumber of between about 1000 and about 1150. The method then progresses to step S1630. At step S1630, a primary acoustic signal is obtained by a sensor, the primary acoustic signal being generated by the target in response to the irradiation of the target with light from the light source. The method then progresses to step S1640. At step S1640, an analyte concentration in the target is estimated based on both of the obtained primary acoustic signal and the measured impedance of the target.

Thermal Monitoring

Thermal monitoring may additionally or alternatively be used to calibrate the photoacoustic sensing technique of the analyte monitor. In particular, measuring the heat conductivity, the specific heat capacity and/or the thermal resistance response of the target concurrently with using the above-described photoacoustic techniques may allow for the detection of variation in the acoustic response caused by changes to the target that are not associated with a change in analyte concentration level.

Using the example of the target being a user and the analyte of interest being glucose, it may be determined that an increasing water content in tissue of the user causes a decrease in the acoustic signal response from the above-described photoacoustic techniques. It may also be determined that an increasing water content in the skin of the user may result in a (for example) higher thermal conductivity of the target, since a higher water content results in a decrease in thermal conductivity.

For the above example, measuring thermal characteristics concurrently with measuring the acoustic signal obtained from the photoacoustic techniques detailed above may allow for a determination that a smaller (or larger) acoustic response is not the result of a respective decrease (or increase) in glucose concentration (which may in some circumstances require some additional action to be taken, such as prompting the user to raise their glucose concentration levels) but is instead the result of an change in skin water content.

In this manner, the analyte monitor described above may be made more accurate.

Figure 17:
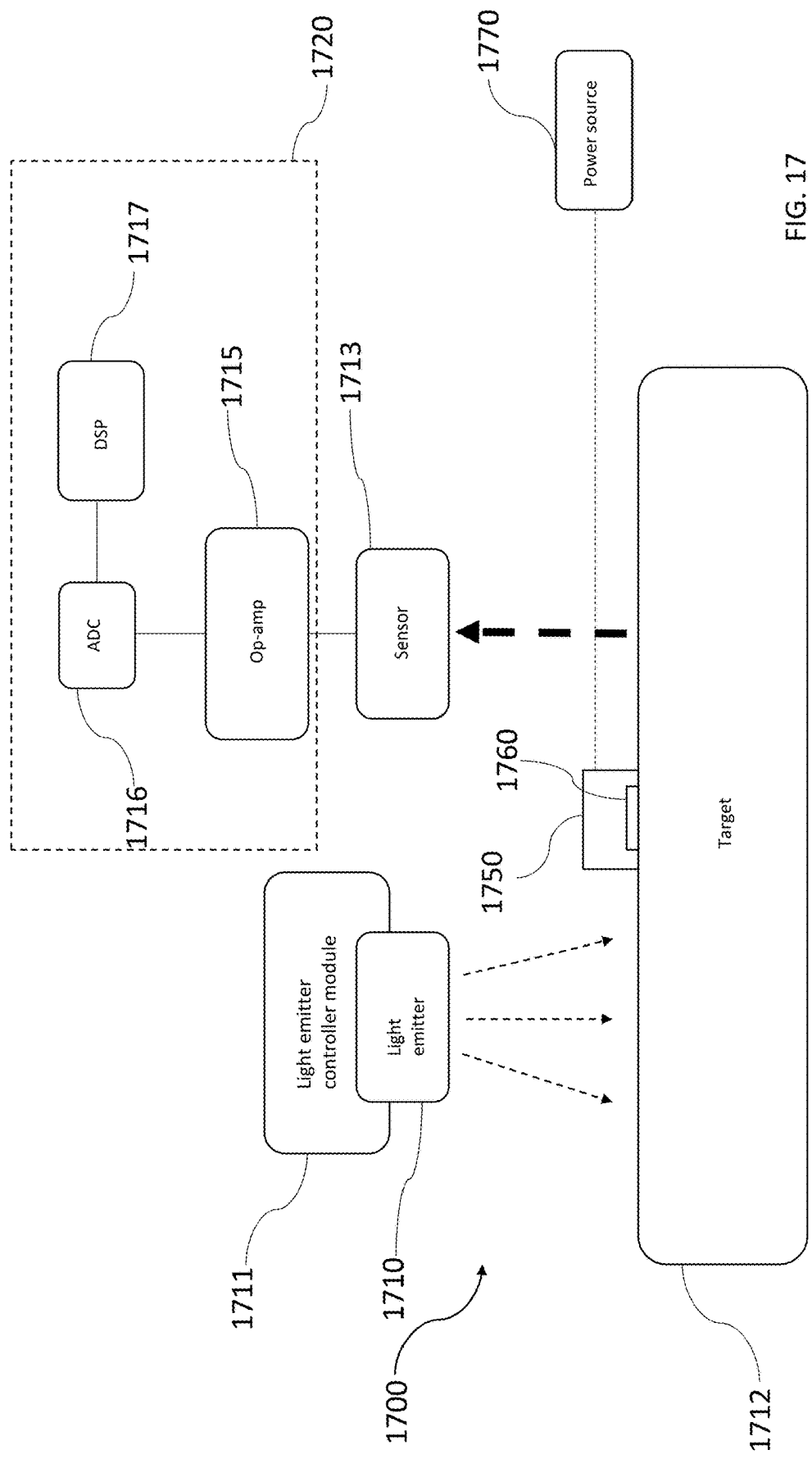
FIG. 17 shows a schematic of an analyte monitor in accordance with exemplary embodiments.

FIG. 17 shows a logical schematic illustrating an analyte monitor including additional elements for thermal characteristic measurement. As can be seen in FIG. 17, the analyte monitor 1700 includes a light emitter 1710 for emitting light (shown with thin dashed lines) towards a target 1712. In an exemplary embodiment, the light emitter 1710 comprises a light-emitting diode (LED). In some embodiments, the light emitter 1710 comprises a laser chip. A light emitter controller module 1711 includes circuitry associated with the light emitter 1710. In exemplary embodiments, the light emitter controller module 1711 is configured to control the light emitter 1710 such that the pulses of light emitted by the light emitter 1710 have a pre-determined or a variable pulse repetition frequency (PRF). In other words, the light emitter controller module 1711 is suitable for modulating the frequency of the light pulses emitted by the light emitter 1710. Preferably, the light emitter controller module 1711 is configured to control the light emitter 1710 so as to emit light pulses having a duration of about 500 ns per pulse at a frequency of about 50 kHz or more. This pulse duration and frequency has been found to achieve a good acoustic response for certain analytes of interest, such as glucose.

The analyte monitor 1700 further includes a sensor 1713, for example a microphone or a transducer, such as a piezo-electric transducer. The sensor 1713 is configured to detect acoustic waves (shown with a bold dashed line) emitted from the thermal excitation of analyte molecules and volumetric expansion in the target 1712 by the light emitted from the light emitter 1710 and generate an electrical signal based on these acoustic waves (which may be referred to as the 'primary acoustic signal').

In exemplary embodiments, the sensor 1713 is operably connected to a signal processor 1720. In the embodiment shown in FIG. 17, the signal processor 1720 includes an operational amplifier ("op-amp") 1715 configured to further amplify the electronic signal derived from the acoustic response of the target 1712. In exemplary embodiments, the op-amp 1715 is operably connected to an analog-to-digital converter 1716 configured to convert the analog electrical signal from the sensor 1713 to a digital signal. In exemplary embodiments, the analog-to-digital converter 1716 is operably connected to a digital signal processor ("DSP") 1717 for processing of the digital signal. It will be appreciated that the above-described components 1710, 1711, 1713 and 1720 of the analyte monitor 1700 may be contained within a singular housing or may be contained separately within different housings.

In exemplary embodiments, the op-amp 1715 is adjustable so as to adjust the gain or amplification amount of the op-amp. In this manner, the amplification of the electronic signal derived from the acoustic response of the target 1712 may be adjusted as desired so as to ensure that this electronic signal is large enough to be accurately measured without causing saturation of this electronic signal.

The analyte monitor further includes a heating element 1750. The heating element 1750 is connected to a power source 1770 and is configured to apply heat to the target. In an exemplary embodiment, the heating element 1750 comprises a thermistor. The analyte monitor further includes a thermal sensor 1760. In the exemplary embodiment shown in FIG. 17, the thermistor acts as both the heating element 1750 and the thermal sensor 1760. In some alternative examples, the thermal sensor is incorporated in or combined with sensor 1713, or may located elsewhere in or separate to the analyte monitor 1700. The heating element 1750 includes circuitry so as to control the application of heat to the target 1712. For example, the heating element 1750 may comprise a resistive element which emits heat when an electrical current is passed through the resistive element. The internal circuitry of the heating element is configured to selectively control the application of the current through the resistive element so as to cause the emission of heat from the resistive element. The internal circuitry of the heating element may be adjustable so to increase or decrease the amount of current supplied to the resistive element, thereby allowing for an adjustment in the amount of heat applied to the target by the heating element.

In use, the heating element 1750 applies heat to the target and the thermal sensor 1760 measures the thermal response of the target. The thermal response is then used to determine if a reduction in the strength of the acoustic response from the thermal excitation of analyte molecules is not due to a decrease in the concentration of analyte molecules but is instead due to some other characteristic of the target changing, such as the water content of the target changing.

In some embodiments, the specific thermal property determined is the specific heat capacity of the target. In some embodiments, the specific thermal property determined is the heat conductivity of the target. Both of the specific heat capacity and the heat conductivity is correlated to the water content of the target. In order to determine these thermal properties from the thermal response of the target, a thermal pulse decay (TPD) technique may be used. In this technique, a thermistor is first used to apply heat to the target for a predetermined period, for example between around 1 second and around 5 seconds. Subsequently, after heating cessation, the same thermistor is then used to measure the temperature decay. The rate of measured temperature decay allows for a determination of the thermal conductivity of the target, following on from Fourier's law that local heat flux density is proportional to the product of thermal conductivity and negative temperature gradient.

In some embodiments, in order to correctly correlate a particular measured thermal response value to a particular characteristic of the target, a training period is implemented to correlate thermal response measurements to target characteristic variations. During this training period, the analyte monitor is installed on the target and thermal response measurements are obtained over a period of several hours or days and monitored for trends together with photoacoustic methods. Using the example of the target being user's tissue and the measured thermal response being thermal conductivity, it may be determined over this time period that the measured thermal response may vary in a particular manner when skin water content is known to increase or decrease. For example, it may be determined that the measured thermal conductivity of the user's skin increases overnight, when the skin's water content is expected to decrease. Over this time period, training and validation data sets of thermal response measurements and photoacoustic measurements are obtained together with target data from another technique of obtaining analyte concentration values (such as a transdermal continuous glucose monitor or via fingerprick testing), in the same manner as described above with respect to FIGS. 7 to 11, with the measured thermal response being a feature "$x_n$," that is taken into account with the other features described with respect to this method.

After the model is fitted, the model is run with the photoacoustic measurements and thermal response measurements of the validation dataset. The results of this run are compared to the target data obtained by the different technique. In this manner, the model can be trained to accurately predict analyte concentration values on the basis of both acoustic signal responses and thermal response measurements. In exemplary embodiments, the fitted model is stored on the DSP 1717.

Figure 18:
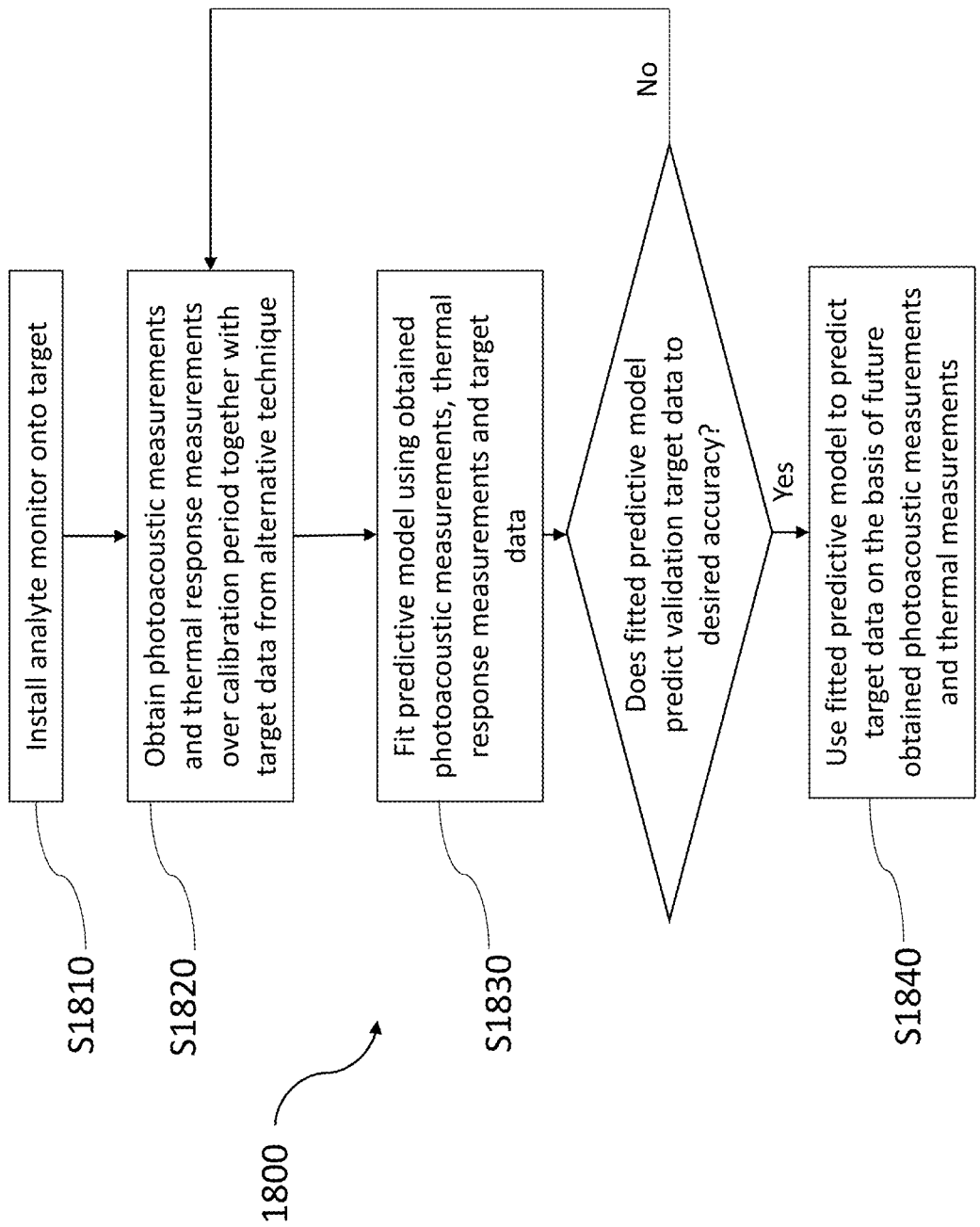
FIG. 18 shows a flowchart of a method of fitting a predictive model in accordance with exemplary embodiments.

FIG. 18 shows a method 1800 for training an analyte monitor including a photoacoustic sensor, a heating element and a thermal sensor. The method starts at step S1810. At step S1810 the analyte monitor is installed onto a target, for example placed on the skin of a user. The method then progresses to step S1820. At step S1820, photoacoustic measurements and thermal response measurements are obtained over an initial calibration period together with another technique for obtaining analyte concentration values over this same period. These measurements are split into a training dataset and a validation dataset. After obtaining photoacoustic measurements, thermal response measurements and analyte concentration measurements, the method progresses to step S1820. At step S1820 a predictive model is fit using the training dataset. In particular, the photoacoustic measurements and thermal response measurements may be used as input vectors of the training dataset, and the analyte concentration measurements may be used as a series of targets of the training dataset. The predictive model assigns various weights to the input vectors so as to better fit the predictive model using the techniques as described above with respect to FIGS. 7 to 11. After the predictive model has been fitted, the method moves onto step S1830.

At step S1830, the fitted predicted model is used to predict targets on the basis of the photoacoustic measurements and the thermal response measurements of the validation dataset. These predicted targets are then compared to the analyte concentration values of the validation dataset. If the fitted predictive model predicts the targets within a pre-determined accuracy threshold, the method progresses to step S1840. If the fitted predictive model does not predict the targets within a pre-determined accuracy, the method reverts to step S1810 for additional training and fitting.

At step S1840, the analyte monitor is fitted and predicts analyte concentration values on the basis of future-obtained photoacoustic measurements and thermal response measurements. There is no longer a need for invasive analyte concentration monitoring techniques.

Figure 19:
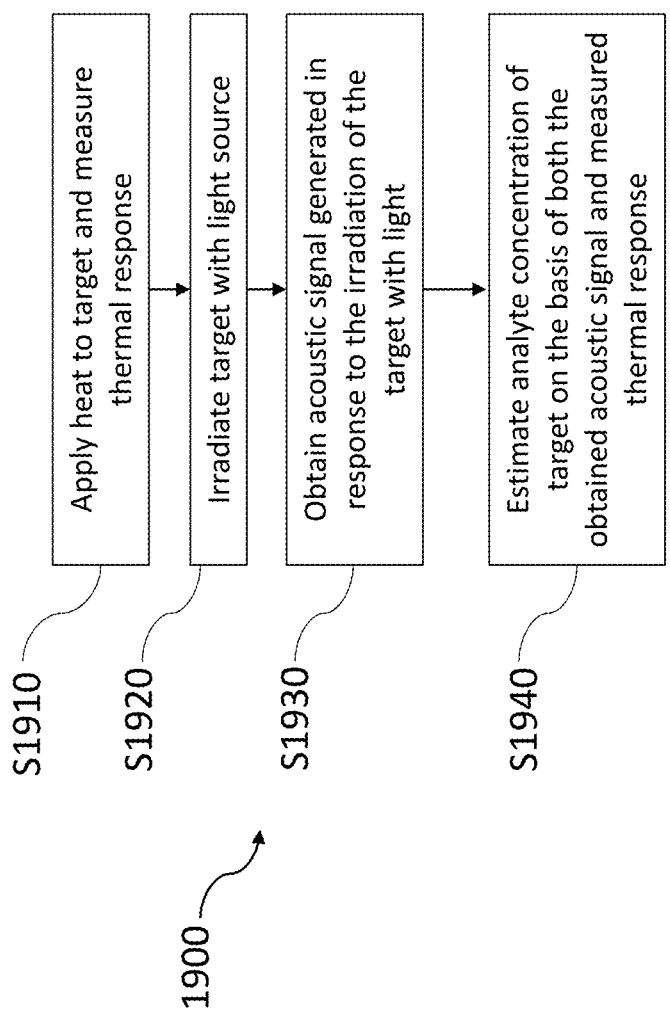
FIG. 19 shows a flowchart of a method in accordance with exemplary embodiments.

FIG. 19 shows a method 1900 for estimating analyte concentration levels in a target using an analyte monitor of the form as detailed above. The method begins at step S1910. At step S1910, heat is applied to a target using a heating element and the thermal response of the target is measured using a thermal sensor. In an embodiment, a thermistor is used as both of the heating element and the thermal sensor. In alternative embodiments, separate heating elements, such as a heating coil, and thermal sensors are provided. The method then progresses to step S1920. At step S1920, the target is irradiated with light of a first wavelength from a light emitter. Preferably, the light of the first wavelength has a wavenumber of between about 1000 and 1150. The method then progresses to step S1930. At step S1930, a primary acoustic signal is generated by a sensor, the acoustic signal being generated by the sensor on the basis of acoustic waves generated by the target in response to the irradiation of the target with light from the light source. The method then progresses to step S1940. At step S1940, an analyte concentration in the target is estimated based on both of the obtained primary acoustic signal and the measured thermal response of the target.

Background Absorption Level

Techniques to determine a background level of light absorption may additionally or alternatively be used to calibrate the photoacoustic sensing technique of the analyte monitor. In particular, measuring the background light absorption level concurrently with using the above-described photoacoustic techniques may allow for the detection of variation in the acoustic response caused by changes to the target that are not associated with a change in analyte concentration.

Using the example of the target being a user and the analyte of interest being glucose, it may be determined that changes in the water content, fibrotic structure or keratin levels of the tissue of the user causes a change in the acoustic signal response from the above-described photoacoustic techniques, even when analyte concentration levels are unchanged. By taking these changes in the acoustic signal response into account, the analyte monitor described above may be made more accurate.

Figure 20:
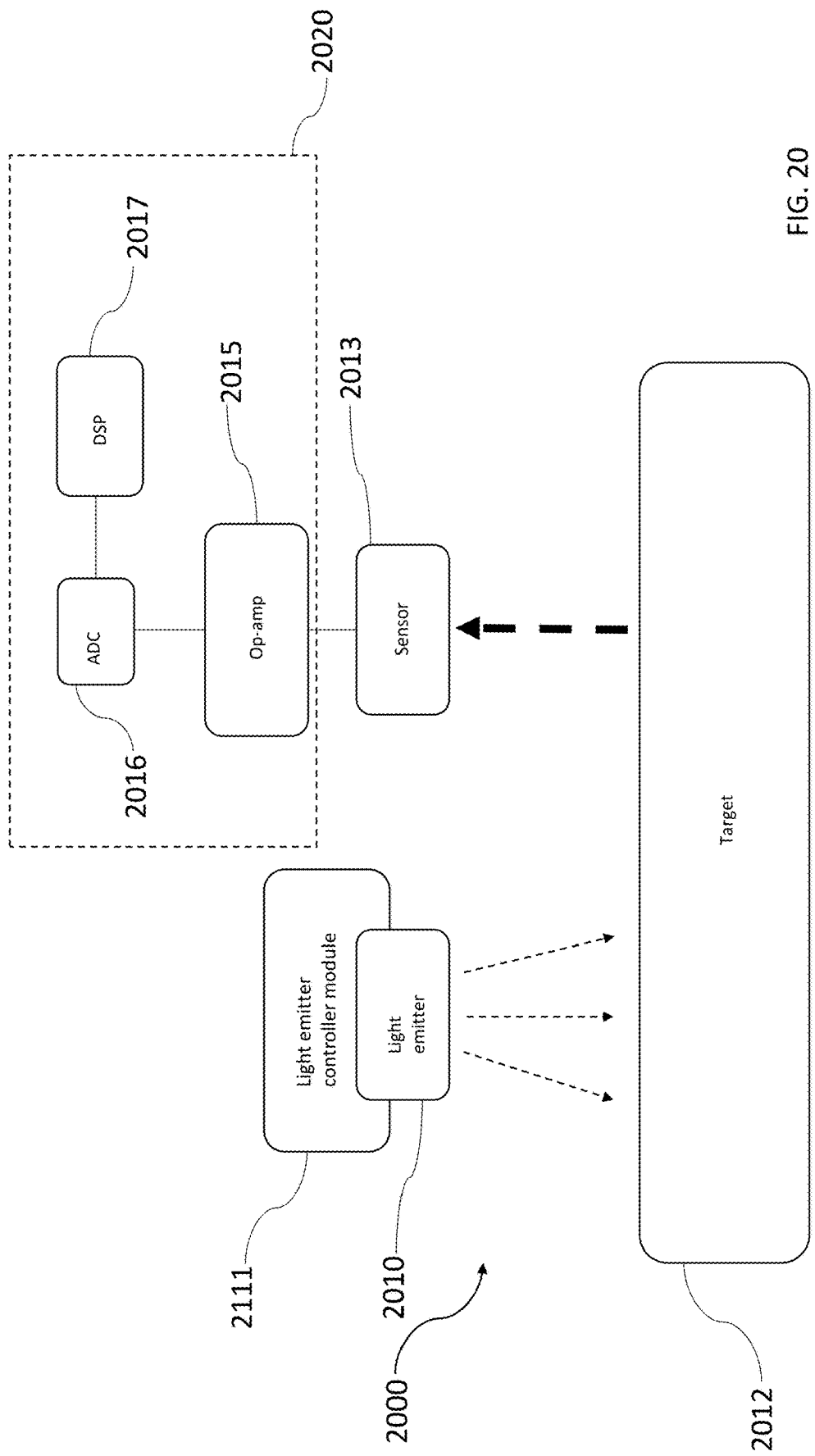
FIG. 20 shows a schematic of an analyte monitor in accordance with exemplary embodiments.

FIG. 20 shows a logical schematic illustrating an analyte monitor including additional elements for the measurement of a background light absorption level. As can be seen in FIG. 20, the analyte monitor 2000 includes a light emitter 2010 for emitting light (shown with thin dashed lines) towards a target 2012. In an embodiment, the light emitter 2010 is configured to emit light of multiple wavelengths. In an embodiment, the light emitter 2010 comprises a tunable laser. In an alternative embodiment, the light emitter 2010 comprises multiple light sources, each of which are configured to emit light of one or more wavelengths (e.g., a single wavelength or different wavelengths). A light emitter controller module 2011 includes circuitry associated with the light emitter 2010. In exemplary embodiments, the light emitter controller module 2011 is configured to control the light emitter 2010 such that the pulses of light emitted by the light emitter 2010 have a pre-determined or a variable pulse repetition frequency (PRF). In other words, the light emitter controller module 2011 is suitable for modulating the frequency of the light pulses emitted by the light emitter 2010.

The analyte monitor 2000 further includes a sensor 2013, for example a microphone or a transducer, such as a piezoelectric transducer. The sensor 2013 is configured to detect acoustic waves (shown with a bold dashed line) emitted from the thermal excitation of analyte molecules and volumetric expansion in the target 2012 by the light emitted from the light emitter 2010 and generate an electrical signal based on these acoustic waves.

In exemplary embodiments, the sensor 2013 is operably connected to a signal processor 2020. In the embodiment shown in FIG. 20, the signal processor 2020 includes an operational amplifier ("op-amp") 2015 configured to further amplify the electronic signal derived from the acoustic response of the target 2012. In exemplary embodiments, the op-amp 2015 is operably connected to an analog-to-digital converter 2016 configured to convert the analog electrical signal from the sensor 2013 to a digital signal. In exemplary embodiments, the analog-to-digital converter 2016 is operably connected to a digital signal processor ("DSP") 2017 for processing of the digital signal. It will be appreciated that the above-described components 2010, 2011, 2013 and 2020 of the analyte monitor 2000 may be contained within a singular housing or may be contained separately within different housings.

In exemplary embodiments, the op-amp 2015 is adjustable so as to adjust the gain or amplification amount of the op-amp. In this manner, the amplification of the electronic signal derived from the acoustic response of the target 2012 may be adjusted as desired so as to ensure that this electronic signal is large enough to be accurately measured without causing saturation of this electronic signal.

In use, the light emitter 2010 is configured to first irradiate the target with light of a second wavelength. The light of the second wavelength has a wavelength that does not strongly interact with the analyte of interest. For example, if the analyte of interest is glucose, the wavelength of the second wavelength may be from around 3,000 nm to around 7,000 nm. An acoustic signal response from the target is then obtained from the photoacoustic effect arising from irradiating the target with second of this first wavelength. After obtaining the acoustic signal response generated from irradiating the target with light of the second wavelength, a background absorption level is determined by the signal processor on the basis of this acoustic signal response.

After determining the background absorption level on the basis of the acoustic signal response associated with irradiating the target with light of the second wavelength, the light emitter 2010 is configured to irradiate the target with light of a first wavelength that strongly interacts with the analyte of interest. For example, if the analyte of interest is glucose, the wavelength of the first wavelength may be a value from around 8,700 nm to around 10,000 nm. The acoustic signal response generated in response to the irradiation of light having this second wavelength is then measured. By taking into account the estimated background absorption level of light determined from the measurement of the acoustic signal response generated in response to the irradiation of the target with light of the second wavelength, the analyte concentration may be determined more accurately from the primary acoustic signal generated on the basis of the acoustic waves generated by the target in response to the irradiation of the target with light of the first wavelength.

Figure 21:
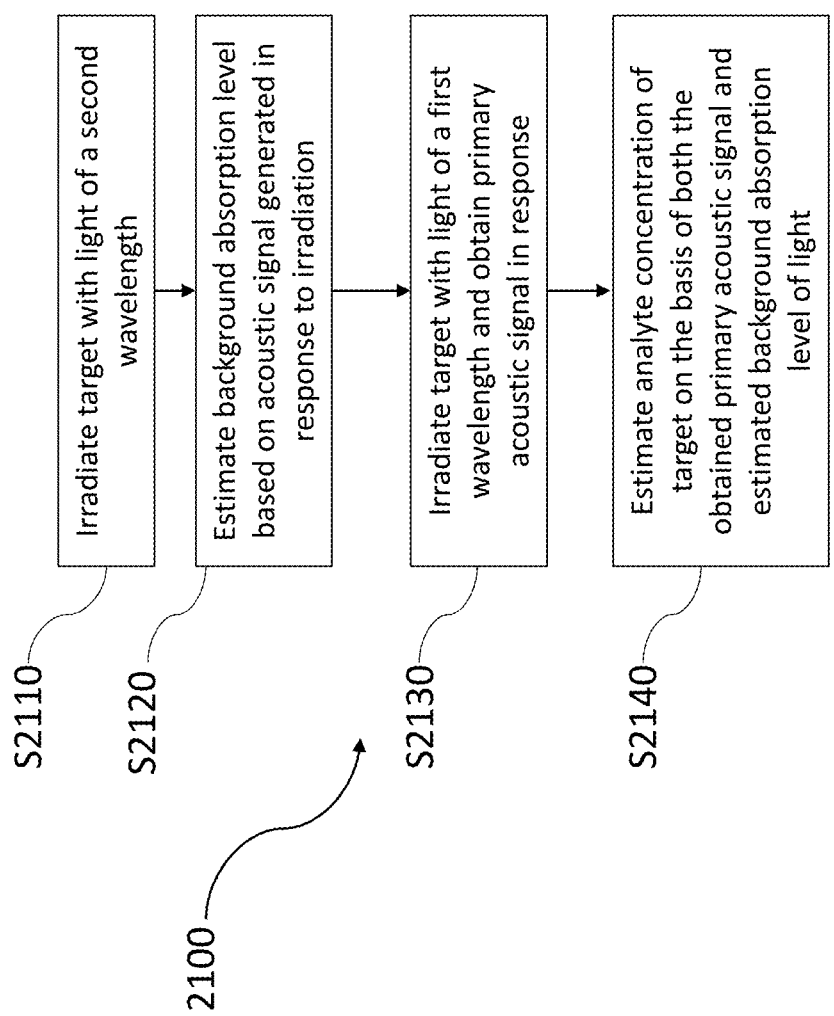
FIG. 21 shows a flowchart of a method in accordance with exemplary embodiments.

FIG. 21 shows a method 2100 for estimating analyte concentration levels in a target using an analyte monitor of the form as detailed above. The method begins at step S2110. At step S2110, the target is irradiated with light of a second wavelength and a secondary acoustic signal response is obtained. The method then progresses to step S2120. At step S2120, a background absorption level of light is estimated on the basis of the secondary acoustic signal response. The method then progresses to step S2130.

At step S2130, the target is irradiated with light of a first wavelength and a primary acoustic signal response is obtained. Preferably, the light of the second wavelength has a wavenumber of between about 1000 and 1150. The method then progresses to step 2140. At step 2140, an analyte concentration in the target is estimated based on both of the obtained second acoustic signal and the estimated background absorption level of light.

The present inventors have also recognized that the acoustic waves generated in response to light of the two different wavelengths of light have the same wavelength. As such, the resonance chamber detailed above would act to amplify both of these acoustic waves, thereby advantageously allowing for an inexpensive sensor to detect both of these acoustic waves.

Alternatively, light of both of the first and second wavelengths may be applied simultaneously to the target in pulses having different pulse repetition frequencies (PRFs). The secondary acoustic signal corresponding to the background absorption level will have a pulse repetition frequency corresponding to the pulse repetition frequency of the pulses of light of the second wavelength. The primary acoustic signal will have a pulse repetition frequency corresponding to the pulse repetition frequency of the pulses of light of the first wavelength. By separating the acoustic signals based on their different pulse repetition frequencies, the background absorption level may be estimated, using the secondary acoustic signal response, simultaneously with obtaining the primary acoustic signal response.

In exemplary embodiments, the pulse repetition frequencies and/or the first and second wavelengths of light are variable. This may be achieved by using one or more tunable lasers as the light emitter 2010. By allowing for variation of the first and second wavelengths of light, the analyte monitor 2000 may be adapted to detect different analytes of interest. For example, if a first analyte of interest was glucose, the wavelength of the first wavelength of light may be selected as a value from around 8,700 nm to around 10,000 nm, which wavelength strongly interacts with glucose molecules, and the second wavelength of light may be chosen as from around 2,500 nm to around 3,000 nm, which wavelength of light interacts relatively less strongly with glucose molecules. If, subsequent to monitoring the concentration levels of glucose, it was desired to monitor a second analyte of interest, the first and second wavelengths may be varied accordingly. For example, if a second analyte of interest was ketone, the wavelength of the first wavelength of light may be changed to a value of from around 2,000 nm to around 2,500 nm, which wavelength strongly interacts with ketone bodies, and the second wavelength of light may be changed to from around 5,000 nm to around 7,000 nm, which wavelength of light interacts relatively less strongly with ketone bodies.

In this manner, the analyte monitor may be adapted so as to accurately determine concentration levels of different analytes of interest.

Combinations of Calibration Techniques

It is to be appreciated that the above three calibration techniques may act synergistically to further improve the accuracy of estimating an analyte concentration measurement. For example, an analyte monitor may include both of a thermistor to monitor thermal responses of the target and electrode probes to perform EIS measurements on the target. Each of the measured thermal response and the measured target impedance will be taken into account as features to train the model. As another example, an analyte monitor may include both of a thermistor to monitor thermal responses of the target and a light emitter capable of emitting multiple wavelengths of light to estimate background absorption levels. Each of the measured thermal response and the estimated background absorption level will be taken into account as features to train the model. As yet another example, an analyte monitor may include both of a light emitter capable of emitting multiple wavelengths of light to estimate background absorption levels and electrode probes to perform EIS measurements on the target. Each of the estimated background absorption level and the measured target impedance will be taken into account as features to train the model. As yet still another example, an analyte monitor may include all of a thermistor to monitor thermal responses of the target, a light emitter capable of emitting multiple wavelengths of light to estimate background absorption levels and electrode probes to perform EIS measurements on the target. All of the measured thermal response, the estimated background absorption level and the measured target impedance will be taken into account as features to train the model. By using all of the measured data in combination, the model described above may be more accurate through the process of fitting, in the manner described above with respect to FIGS. 8 to 11. In particular, the inclusion of multiple different sets of data may be used to improve the training and validation data sets of photoacoustic measurements in the manner described above with respect to FIGS. 7 to 11, with each set of sensor data being individual features "$x_n$" that is taken into account with the other features described with respect to this method.

In an embodiment, each of the above techniques and combinations of techniques corresponds to modes selectable by a user of the analyte monitor. For example, the analyte monitor may have seven modes: (1) a mode corresponding to measuring a thermal response of the target; (2) a mode corresponding to measuring a background level of absorption of the target; (3) a mode corresponding to measuring an electrical impedance of the target; (4) a mode corresponding to measuring a thermal response of the target and measuring a background level of absorption of the target; (5) a mode corresponding to measuring a thermal response of the target and measuring an electrical impedance of the target; (6) a mode corresponding to measuring a background level of absorption of the target and measuring an electrical impedance of the target; and (7) a mode corresponding to measuring a thermal response of the target, measuring a background level of absorption of the target and measuring an electrical impedance of the target. It will be appreciated that the analyte monitor may include less than seven modes, corresponding to a selection of various modes of the modes listed above. During the selection of a mode in which multiple techniques are being used, the components involved in each technique may be used simultaneously, concurrently or serially.

Figure 22:
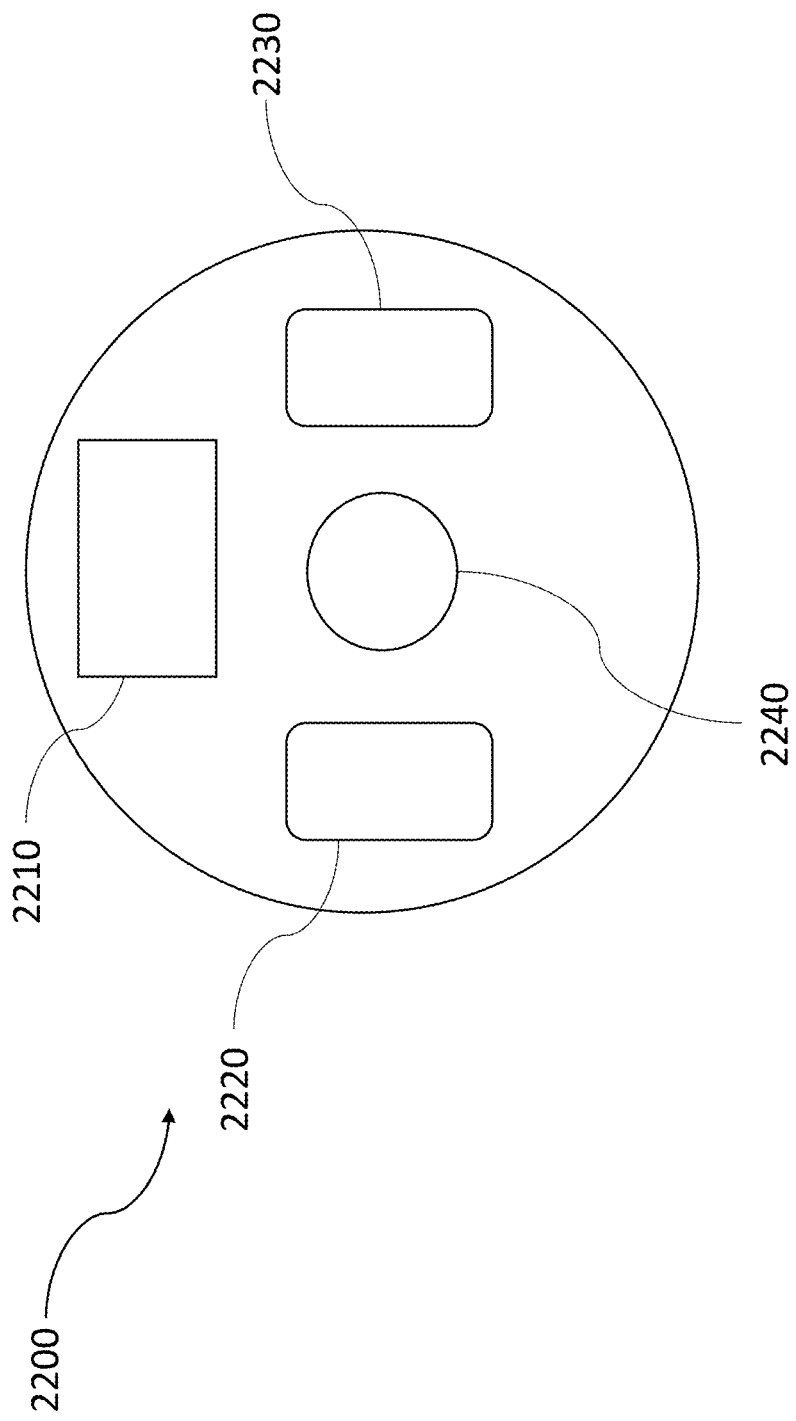
FIG. 22 shows a bottom view of an analyte monitor in accordance with exemplary embodiments.

For example, FIG. 22 shows a bottom view of an analyte monitor 2200 including features to allow for the performance of mode (7) listed above, in which all three of the above-described calibration techniques are used. In particular, the analyte monitor includes a thermal sensor 2210 for measuring thermal responses of a target. In some examples, the thermal sensor 2210 is a thermistor. The analyte monitor further includes first and second electrodes 2220 and 2230 for application of a voltage so as to measure the impedance of a target. The analyte monitor 2200 further includes a photoacoustic window 2240 through which light is emitted so as to be incident on the target. The analyte monitor 2200 includes a light emitter capable of emitting light of two different wavelengths so as to estimate the background level of absorption. In exemplary embodiments, these three calibration techniques are performed simultaneously, concurrently or serially, and the model is fitted with data obtained from each of these calibration techniques.

Reverse Iontophoresis

Techniques in accordance with this disclosure are available to improve the strength of the acoustic signal received by the analyte monitor. One such technique is the use of reverse iontophoresis.

Reverse iontophoresis may be used as a technique for estimation of an analyte concentration level. In particular, reverse iontophoresis may be used to extract an analyte of interest though the skin of a user via application of an electric field to a user and then drawing out the analyte of interest via electro-osmotic flow, and has previously been demonstrated for monitoring glucose concentration levels.

However, the present inventors recognized that the effect inherent in reverse iontophoresis of drawing glucose molecules towards the surface of a user's skin may be used to increase the acoustic signal strength obtained via irradiation of the user's skin with light.

In particular, by drawing the analyte of interest closer to the user's skin, any acoustic signal response generated by the analyte of interest in response to being irradiated with light is less likely to be attenuated by other structures or molecules in the user's skin. Reverse iontophoresis is therefore not itself used to monitor glucose concentration levels but is instead used to increase the signal strength obtained by the photoacoustic techniques as described above.

Figure 23:
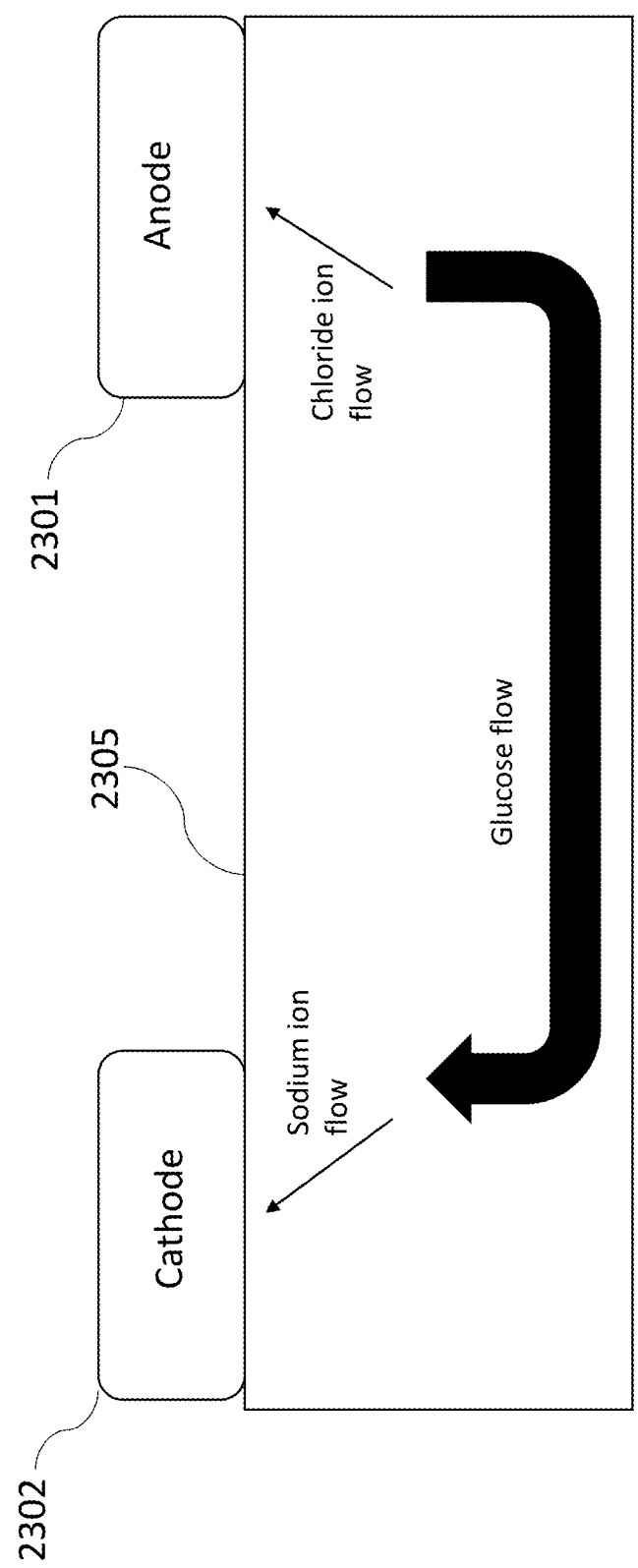
FIG. 23 shows a diagram explaining the technique of reverse iontophoresis.

FIG. 23 shows a diagrammatic explanation of reverse iontophoresis. As can be seen in the diagram, two electrodes 2301, 2302 are placed into contact with the user's skin 2305. The anode electrode 2301 draws negative ions, such as chloride ions, towards it. The cathode electrode 2302 draws positive ions, such as sodium ions, towards it. The flow of the sodium ions draws water molecules towards the cathode. Glucose molecules are also forced, under osmotic pressure, toward the cathode.

By positioning the cathode proximate to the area of the user's skin which is irradiated with light, the strength of the acoustic signal response from the glucose molecules is increased. This increased strength of acoustic signal response has an improved signal to noise ratio, and the subsequent estimation of the analyte concentration level is therefore improved.

Figure 24:
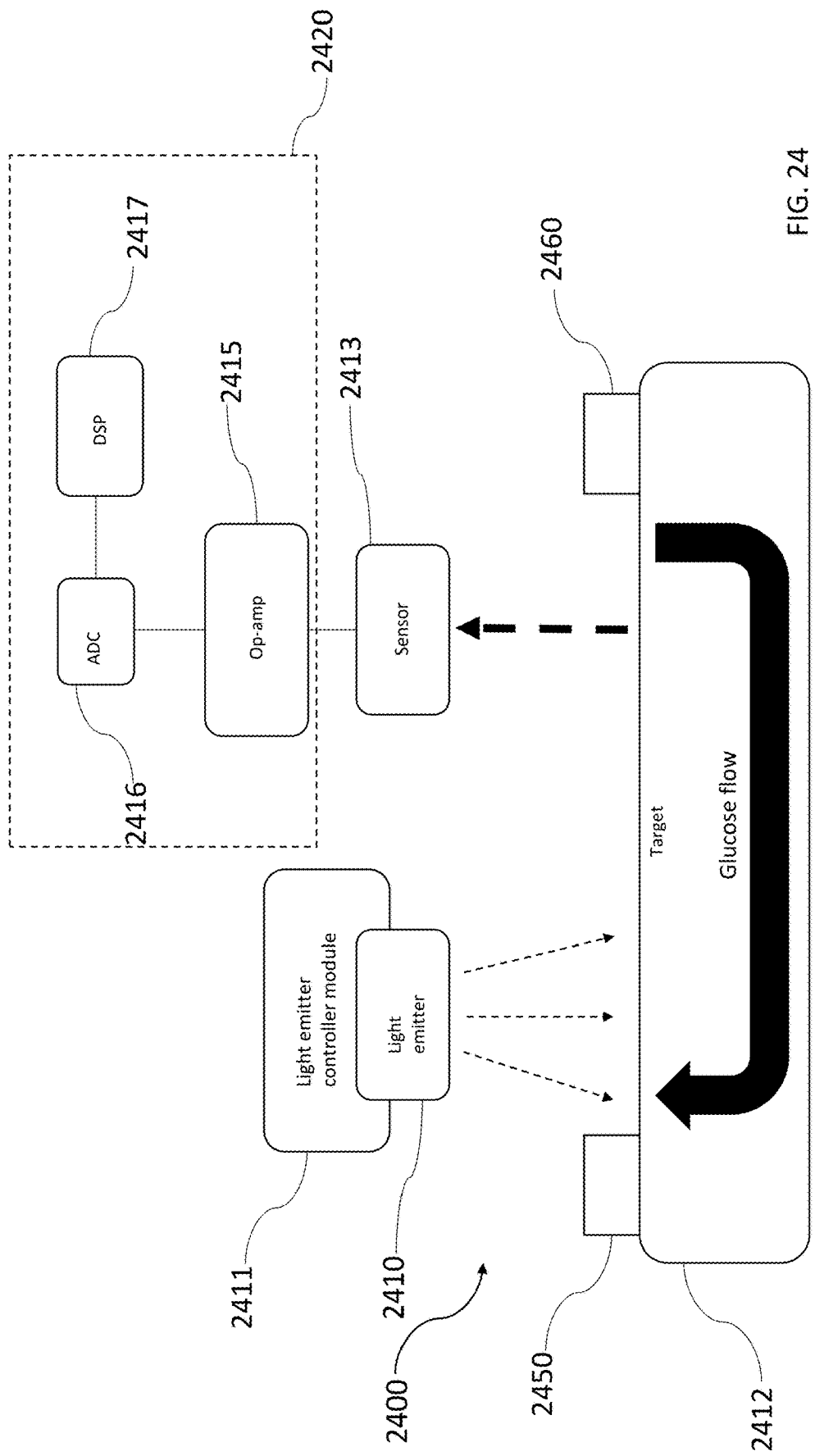
FIG. 24 shows a schematic of an analyte monitor in accordance with exemplary embodiments.

FIG. 24 shows a logical schematic of an analyte monitor including electrodes for performing reverse iontophoresis concurrently with performing photoacoustic techniques as described above. As can be seen in FIG. 24, the analyte monitor 2400 includes a light emitter 2410 for emitting light (shown with thin dashed lines) towards a target 2412. In an exemplary embodiment, the light emitter 2410 comprises a light-emitting diode (LED). In an alternative embodiment, the light emitter 2410 comprises a laser chip. A light emitter controller module 2411 includes circuitry associated with the light emitter 2410. In exemplary embodiments, the light emitter controller module 2411 is configured to control the light emitter 2410 such that the pulses of light emitted by the light emitter 2410 have a pre-determined or a variable pulse repetition frequency (PRF). In other words, the light emitter controller module 2411 is suitable for modulating the frequency of the light pulses emitted by the light emitter 2410. In some examples, the light emitter controller module 2411 is configured to control the light emitter 2410 so as to emit light pulses having a duration of from about 400 ns to about 600 ns, for example about 500 ns per pulse at a frequency of from about about 40 kHz to about 60 kHz, for example about 50 kHz. This pulse duration and frequency has been found to achieve a good acoustic response for certain analytes of interest, such as glucose.

The analyte monitor 2400 further includes a sensor 2413, for example a microphone or a transducer, such as a piezo-electric transducer. The sensor 2413 is configured to detect acoustic waves (shown with a bold dashed line) emitted from the thermal excitation of analyte molecules and volumetric expansion in the target 2412 by the light emitted from the light emitter 2410 and generate an electrical signal based on these acoustic waves.

The analyte monitor further includes a first electrode 2450 and a second electrode 2460. The first and second electrodes are connected to a power source and a voltage controller (not shown). The voltage controller is configured to bias the first and second electrodes. In an embodiment, the first electrode is negatively biased by the voltage controller to act as a cathode (e.g., as described above with reference to FIG. 23) and the second electrode is positively biased by the voltage controller to act as an anode (e.g., as described above with reference to FIG. 23). The cathode is positioned proximate to the area on the target irradiated by the light emitted from the light emitter 2410.

In use, glucose molecules are drawn towards the area on the target irradiated by the light emitted from the light emitter 2410 in the manner as described above. In this manner, an increase in the magnitude of the acoustic signal generated by the irradiation of the target with light is obtained.

As will be appreciated by the skilled person, if the analyte monitor 2400 is being used to monitor a concentration level of another analyte of interest instead of glucose, the positions of the first and second electrodes 2450, 2460 may be reversed if the analyte of interest will be drawn instead towards the anode.

In an embodiment, the first and second electrodes 2450, 2460 are spaced apart by a distance of less than about 3 cm. In an embodiment, the first and second electrodes 2450, 2460 comprise a hydrogel pad on their surfaces, the hydrogel pad being configured to contact the target surface. Alternatively, the first and second electrodes 2450, 2460 may be bare metal electrodes, with the metal of these electrodes being configured to contact the target surface. Further alternatively, the first and second electrodes may be needle electrodes (e.g., microneedles).

In an embodiment, the current density of the current applied by the first and second electrodes may be altered so as to ensure this current density falls beneath a pain threshold of a user. For example, the current density may be set at around 1 mA/cm$^2$.

Figure 25:
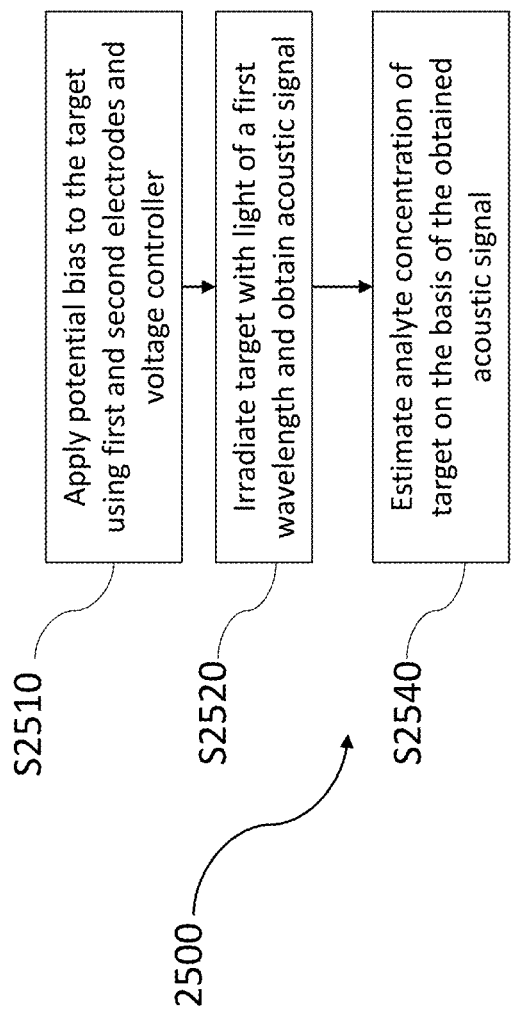
FIG. 25 shows a flowchart of a method in accordance with exemplary embodiments.

FIG. 25 shows a method 2500 for estimating analyte concentration levels in a target using an analyte monitor of the form as detailed above. The method begins at step S2510. At step S2510, a potential bias is applied to the target using electrodes and a voltage controller. The method then progresses to step S2520. At step S2520, the target is irradiated with light of a first wavelength and a primary acoustic signal response is obtained. The method then progresses to step S2530.

At step S2530, an analyte concentration in the target is estimated based on the obtained primary acoustic signal.

Other Analytes of Interest

In addition to the monitoring of glucose, the above techniques have been found to be effective in the monitoring of other analytes of interest, for example ketones. Ketone bodies are a marker for diabetic ketoacidosis (DKA), which is a life-threatening condition that is caused by lack of insulin or elevated blood glucagon levels. By selecting the first wavelength of light emitted by the light emitter to a wavelength that strongly interacts with ketone molecules (e.g., between around 2000 nm and around 2500 nm), the above techniques may be applied for estimating the concentration level of ketone bodies.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An analyte monitor comprising:
a light emitter to emit light toward a target;
a sensor to sense acoustic waves generated by analyte molecules in the target in response to the light emitted by the light emitter;
a cathode and an anode configured to come in contact with the target, wherein an area on the target on which the light emitted by the light emitter is incident is closer to the cathode than to the anode;
a voltage controller coupled to the cathode and the anode to bias the cathode and the anode; and
a signal processor configured to estimate a concentration level of an analyte based on the acoustic waves sensed by the sensor.

2. The analyte monitor of claim 1, wherein the cathode and the anode comprise hydrogel pads configured to come in contact with a surface of the target.

3. The analyte monitor of claim 1, further comprising an electrical impedance spectroscopy (EIS) circuit configured to measure an impedance of the target on a path between the cathode and the anode, wherein the signal processor is configured to estimate the concentration level of the analyte based on the acoustic waves sensed by the sensor and the impedance of the target.

4. The analyte monitor of claim 1, wherein the analyte is glucose, and wherein biasing the cathode and the anode draws glucose molecules towards the cathode, thereby increasing a strength of the acoustic waves.

5. The analyte monitor of claim 1, wherein the light emitter emits light having a wavelength in the mid-infrared region.

6. The analyte monitor of claim 1, wherein the voltage controller is controlled to bias the cathode and the anode so as to produce a current density of less than 1 mA/cm$^2$.

7. The analyte monitor of claim 1, wherein the sensor comprises a transducer.

8. The analyte monitor of claim 1, wherein the sensor comprises a microphone.

9. The analyte monitor of claim 1, further comprising a resonance chamber configured to form a standing wave from generated acoustic waves.

10. The analyte monitor of claim 9, wherein the sensor is positioned proximate to an anti-node of the standing wave to be formed in the resonance chamber.

11. The analyte monitor of claim 9, wherein the resonance chamber comprises a resonance branch for formation of the standing wave and a measurement branch connecting the resonance branch to the sensor, the measurement branch being positioned proximate to an anti-node of the standing wave to be formed in the resonance branch.

12. A method for estimating analyte concentration levels of a specific analyte in a target, the method comprising:
emitting light, using a light emitter, toward an area on the target;
applying, using an anode, a cathode, and a voltage controller, a potential bias across the area on the target, wherein the cathode is positioned closer to the area on the target than the anode;
sensing, using a sensor, acoustic waves generated by analyte molecules in the target in response to the light emitted by the light emitter and generating a primary acoustic signal based on the sensed acoustic waves; and
estimating, using a signal processor, an analyte concentration level based on the primary acoustic signal.

13. The method of claim 12, further comprising:
measuring an impedance of the target on a path between the anode and the cathode,
wherein estimating the analyte concentration level comprises estimating, using the signal processor and a model that uses the primary acoustic signal and the impedance of the target as inputs, the analyte concentration level based on the primary acoustic signal and the impedance of the target.

14. The method of claim 12, wherein the specific analyte is glucose, and wherein the potential bias draws glucose molecules towards the cathode, thereby increasing a strength of the acoustic waves.

15. The method of claim 12, wherein the potential bias produce a current density of less than 1 mA/cm$^2$.

16. The method of claim 12, wherein the emitted light has a wavelength in the mid-infrared region.

17. The method of claim 12, further comprising forming a standing wave from generated acoustic signals in a resonance chamber.

18. The method of claim 17, wherein the sensor is positioned proximate to an anti-node of the standing wave to be formed in the resonance chamber.

19. The method of claim 12, wherein the sensor comprises a transducer.

20. The method of claim 12, wherein the sensor comprises a microphone.

* * * * *